US012232864B2

(12) United States Patent
Matusik et al.

(10) Patent No.: US 12,232,864 B2
(45) Date of Patent: Feb. 25, 2025

(54) SYSTEMS AND METHODS FOR ESTIMATING 3D POSITION AND MOVEMENT FROM TACTILE SIGNALS

(71) Applicant: Massachusetts Institute of Technology, Cambridge, MA (US)

(72) Inventors: Wojciech Matusik, Lexington, MA (US); Antonio Torralba, Somerville, MA (US); Michael J. Foshey, Quincy, MA (US); Wan Shou, Allston, MA (US); Yiyue Luo, Cambridge, MA (US); Pratyusha Sharma, Cambridge, MA (US); Yunzhu Li, Cambridge, MA (US); Tomas Palacios, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 640 days.

(21) Appl. No.: 17/226,564

(22) Filed: Apr. 9, 2021

(65) Prior Publication Data

US 2021/0315485 A1 Oct. 14, 2021

Related U.S. Application Data

(60) Provisional application No. 63/007,675, filed on Apr. 9, 2020.

(51) Int. Cl.
*A61B 5/11* (2006.01)
*A61B 5/00* (2006.01)

(52) U.S. Cl.
CPC .............. *A61B 5/11* (2013.01); *A61B 5/6804* (2013.01); *A61B 5/6892* (2013.01);
(Continued)

(58) Field of Classification Search
CPC ....... A61B 5/11; A61B 5/6804; A61B 5/6892; A61B 5/7246; A61B 5/7264;
(Continued)

(56) References Cited

U.S. PATENT DOCUMENTS 8,925,393 B2  1/2015  Cannard et al.
9,448,127 B2  9/2016  Cannard et al.
(Continued)

FOREIGN PATENT DOCUMENTS

EP    3447463 B1    10/2019
WO    2020081557 A1    4/2020
WO    2020094628 A1    5/2020

OTHER PUBLICATIONS

Kerr, Emmett, T. Martin McGinnity, and Sonya Coleman. "Material recognition using tactile sensing." Expert Systems with Applications 94 (2018): 94-111. (Year: 2018).*
(Continued)

*Primary Examiner* — Alex M Valvis
*Assistant Examiner* — Nidhi N Patel
(74) *Attorney, Agent, or Firm* — Barnes & Thornburg LLP

(57) ABSTRACT

Systems and methods are provided for estimating 3D poses of a subject based on tactile interactions with the ground. Test subject interactions with the ground are recorded using a sensor system along with reference information (e.g., synchronized video information) for use in correlating tactile information with specific 3D poses, e.g., by training a neural network based on the reference information. Then, tactile information received in response to a given subject interacting with the ground can be used to estimate the 3D pose of the given subject directly, i.e., without reference to corresponding reference information. Certain exemplary embodiments use a sensor system in the form of a pressure (Continued)

sensing carpet or mat, although other types of sensor systems using pressure or other sensors can be used in various alternative embodiments.

9 Claims, 28 Drawing Sheets
(16 of 28 Drawing Sheet(s) Filed in Color)

(52) U.S. Cl.
CPC .......... *A61B 5/7246* (2013.01); *A61B 5/7264* (2013.01); *A61B 5/7455* (2013.01); *A61B 5/746* (2013.01); *A61B 2562/0247* (2013.01)

(58) Field of Classification Search
CPC ..... A61B 5/7455; A61B 5/746; A61B 5/6805; A61B 5/6806; A61B 5/6807; A61B 2562/0247; A61B 2562/046; A61B 2560/0223
See application file for complete search history.

(56) References Cited

U.S. PATENT DOCUMENTS

| | | | |
|---|---|---|---|
| 9,642,470 B2* | 5/2017 | Taylor | A47C 27/082 |
| 10,081,887 B2 | 9/2018 | Manipatruni et al. | |
| 10,119,208 B2 | 11/2018 | McMaster | |
| 10,895,026 B2 | 1/2021 | Hamdani | |
| 10,934,639 B2 | 3/2021 | Horter et al. | |
| 2007/0083096 A1 | 4/2007 | Paradiso | |
| 2016/0135744 A1* | 5/2016 | Sarrafzadeh | A61B 5/7278 702/41 |
| 2017/0079868 A1 | 3/2017 | Reid, Jr. et al. | |
| 2018/0008196 A1* | 1/2018 | Connor | A61B 5/1126 |
| 2019/0117124 A1* | 4/2019 | Hsu | A61B 5/6892 |
| 2020/0123689 A1 | 4/2020 | Zhang et al. | |
| 2022/0374569 A1 | 11/2022 | Shou et al. | |

OTHER PUBLICATIONS

Lee, Han Bit, et al. "3D customized and flexible tactile sensor using a piezoelectric nanofiber mat and sandwich-molded elastomer sheets." Smart Materials and Structures 26.4 (2017): 045032. (Year: 2017).*
Liu, Shuangjun, Yu Yin, and Sarah Ostadabbas. "In-bed pose estimation: Deep learning with shallow dataset." IEEE journal of translational engineering in health and medicine 7 (2019): 1-12. (Year: 2019).*
Acharya, Debaditya, Kourosh Khoshelham, and Stephan Winter. "BIM-PoseNet: Indoor camera localisation using a 3D indoor model and deep learning from synthetic images." ISPRS journal of photogrammetry and remote sensing 150 (2019): 245-258. (Year: 2019).*
Engler et. al, Matrix elasticity directs stem cell lineage specification. Cell 1261, 677 (2006).
Dahiya, et. al, Tactile sensing-from humans to humanoids. IEEE Trans. Robot 26, 1 (2009).
Winter, Human balance and posture control during standing and walking. Gait posture 3, 193 (1995).
Someya, et. al, The rise of plastic bioelectronics. Nature 540, 379 (2016).
Yousef, et. al, Tactile sensing for dexterous in-hand manipulation in robotics—A review. Sens. Actuator A Phys. 167, 171 (2011).
Yang, et al., The grand challenges of Science Robotics. Sci. Robot. 3, 14 (2018).
Poupyrev, et. al, Project Jacquard: interactive digital textiles at scale. Proceedings of the 2016 CHI Conference on Human Factors in Computing Systems (ACM, 2016), pp. 4216-4227.
Moeslund, et. al, A survey of advances in vision-based human motion capture and analysis. Comput. Vis. Image Underst. 104, 90 (2006).
Sundaram et. al, Nature 569, 698 (2019).

Zeng, et. al, Fiber-based wearable electronics: a review of materials, fabrication, devices, and applications. Adv. Mater. 26, 5310 (2014).
Yan, et. al, Advanced multimaterial electronic and optoelectronic fibers and textiles. Adv. Mater. 31, 1802348 (2019).
Rein, et. al, Diode fibres for fabric-based optical communications. Nature 560, 214 (2018).
Rogers, et. al, Materials and mechanics for stretchable electronics. science 327, 1603 (2010).
Kim, et al., Stretchable and foldable silicon integrated circuits. Science 320, 507 (2008).
Wang, et. al, Skin-inspired electronics: an emerging paradigm. Acc. Chem. Res. 51, 1033 (2018).
Ahn, et al., Omnidirectional printing of flexible, stretchable, and spanning silver microelectrodes. Science 323, 1590 (2009).
Truby et. al, Printing soft matter in three dimensions. Nature 540, 371 (2016).
Adams, A closed-loop theory of motor learning. J Mot. Behav. 3, 111 (1971).
Wang, et. al, A review of wearable technologies for elderly care that can accurately track indoor position, recognize physical activities and monitor vital signs in real time. Sensors 17,341 (2017).
Narayanan, et. al, Visual knitting machine programming. ACM Transactions on Graphics (TOG) 38, I (2019).
Seiki, Sds-one apex3, [Online]. Available from: http://www.shimaseiki.com/product/design/sdsone_apex/flat/ (2011).
Briseno, et al., Patterning organic single-crystal transistor arrays. Nature 444, 913 (2006).
Khang, et. al, A stretchable form of single-crystal silicon for high-performance electronics on rubber substrates. Science 311, 208 (2006).
Ulyanov, et. al, Deep image prior. Proceedings of the IEEE Conference on Computer Vision and Pattern Recognition (2018), pp. 9446-9454.
D' Alessio, Measurement errors in the scanning of piezoresistive sensors arrays. Sens. Actuator A Phys. 72, 71 (1999).
L. v. d. Maaten, et. al, Visualizing data using t-SNE. J Mach. Learn. Res. 9, 2579 (2008).
Lederman, et. al, Haptic perception: A tutorial. Atten. Percept. Psychophys. 71, 1439 (2009).
Bauby, et. al, Active control of lateral balance in human walking. J Biomech. 33, 1433 (2000).
Okamura, et. al, An overview of dexterous manipulation. Proceedings 2000 ICRA. Millennium Conference. IEEE International Conference on Robotics and Automation. Symposia Proceedings (Cat. No. 00CH37065) (IEEE, 2000), vol. 1, pp. 255-262.
Cho, et. al, Learning phrase representations using RNN encoder-decoder for statistical machine translation. arXiv preprint arXiv: 1406.1078 (2014).
Johansson, et. al, Coding and use of tactile signals from the fingertips in object manipulation tasks. Nat. Rev. Neurosci. 10, 345-359 (2009).
Bartolozzi, et. al, Robots with a sense of touch. Nat. Mater. 15, 921-925 (2016).
Stoll, MI plus pattern software, [Online]. Available from: http://www.stoll.com/stoll_software_solutions_en_4/pattern_software_ml plus/3_I (2011).
Wu, et. al., Stitch meshing. ACM Transactions on Graphics (TOG) 37, I (2018).
Pointner, et al., "Knitted RESi: A Highly Flexibe, Force-Sensitive Knitted Textiles Based on Resistive Yarns". Special Interest Group on Computer Graphics and Interactive Techniques Conference. Aug. 2020.
Cao, et. al, "Realtime Multi-Person 2D Pose Estimation using Part Affinity Fields." Proceedings of the IEEE Conference on Computer Vision and Pattern Recognition (CVPR), 7291-7299, 2017.
Cao, et. al, OpenPose: Realtime Multi-Person 2D Pose Estimation using Part Affinity Fields. arXiv preprint arXiv. 1812.08008, 2018.
Kingma, et. al, "Adam: A Method for Stochastic Optimization." arXiv preprint arXiv. 1412.6980, 2014.
Paszke, et al. "Pytorch: An Imperative Sytle, High-Performance Deep Learning Library." Adv. Neural Infor. Proces. Systems. 2019.

* cited by examiner

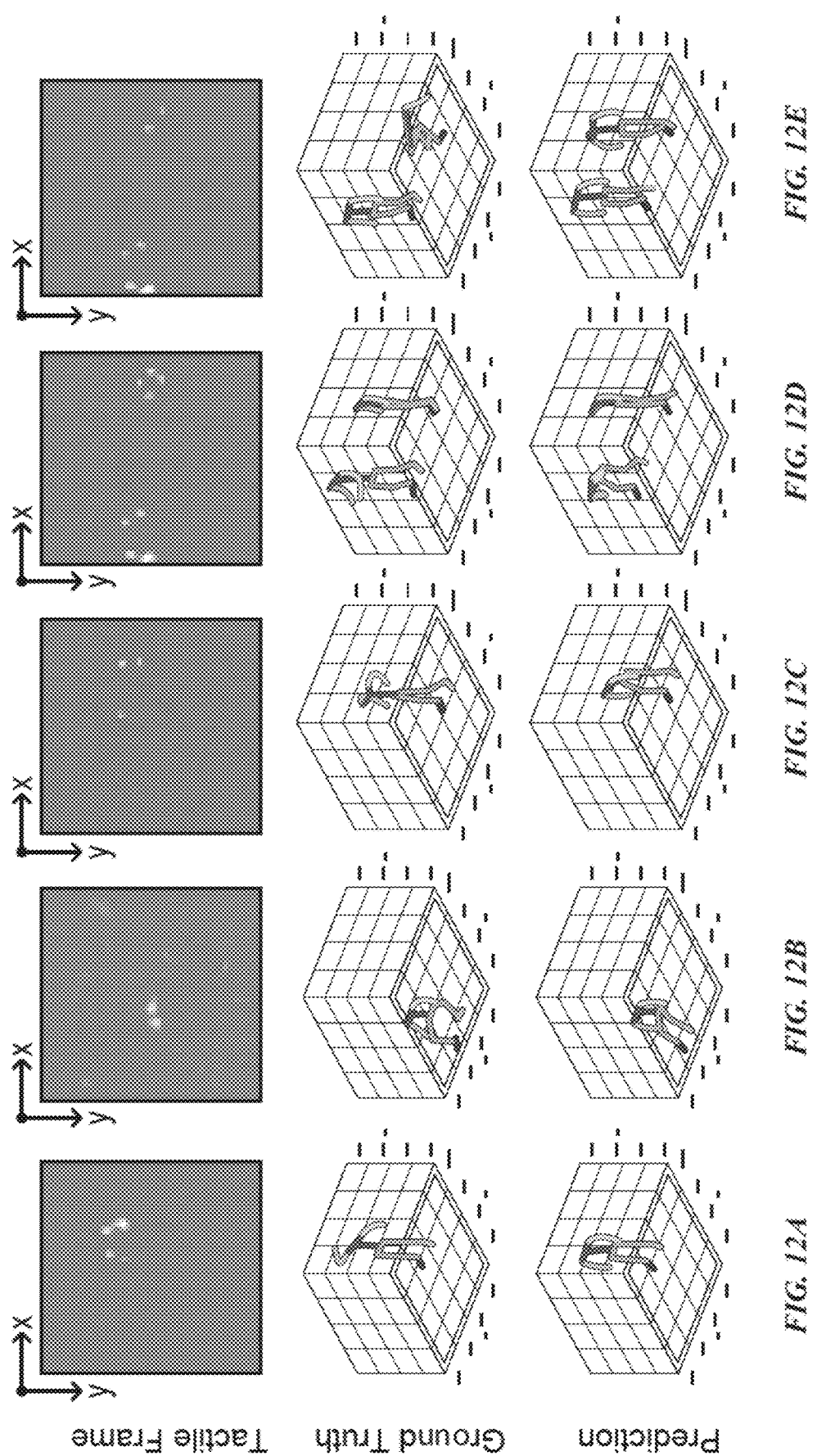

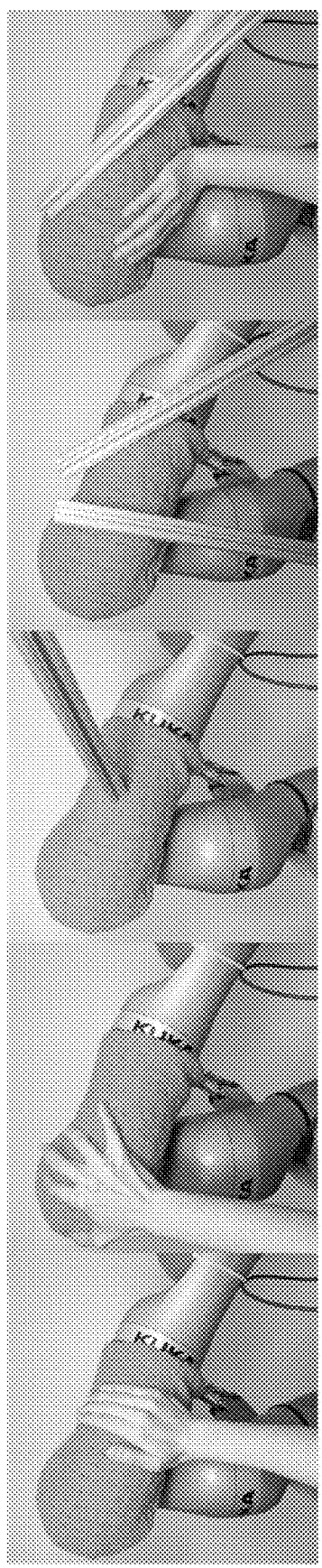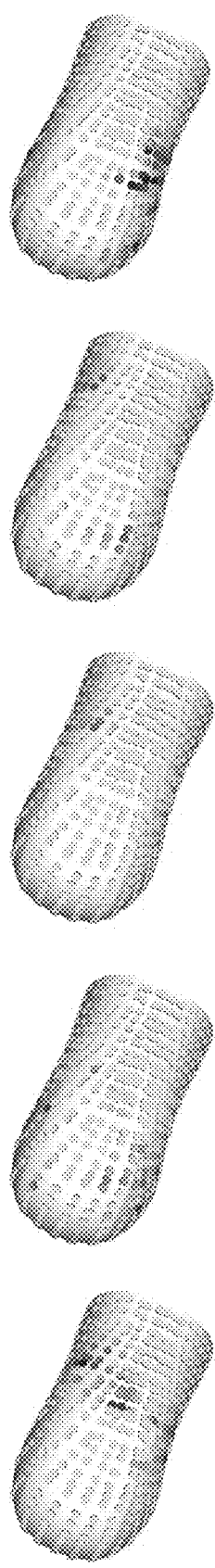
FIG. 18

SYSTEMS AND METHODS FOR ESTIMATING 3D POSITION AND MOVEMENT FROM TACTILE SIGNALS

CROSS-REFERENCE TO RELATED APPLICATION(S)

This patent application claims the benefit of U.S. Provisional Patent Application No. 63/007,675, entitled "SYSTEMS AND METHODS FOR ENABLING HUMAN ACTIVITY LEARNING BY MACHINE-KNITTED, WHOLE-GARMENT SENSING WEARABLES," and filed Apr. 9, 2020, which is hereby incorporated herein by reference in its entirety.

FIELD

The present disclosure relates to manufacturing whole-garment sensing wearables, and more particularly provides for knitting techniques that allow for automated processes to produce such wearable on a large scale. The whole-garment sensing wearables enable human activity learning not achievable by existing smart textiles.

BACKGROUND

Organisms in nature extract information and learn from the external environment through constant physical interactions. As an example, humans leverage their powerful tactile sensory system (skin on hands, limbs, and torso) to perform complex tasks, including dexterous grasp and locomotion. Humans interact with the external environment every day through rich tactile perception. This important sensing modality remains, however, challenging for robots to replicate, as skin-like sensory interfaces are still highly limited in terms of performance, scalability, and cost. Monitoring and understanding of interactions between humans and the physical world provide fundamental knowledge for human behavior study, and to improve health care, biomimetic robots, human-computer interactions, augmented virtual/virtual reality (AV/VR), and others. Whereas visual and audio-based datasets are commonly used to track and analyze human-environment interactions, equivalent rich tactile datasets are rare.

Recently, the coupling of tactile information and machine learning tools has enabled the discovery of signatures of human grasping. However, recording and analysis of whole-body interactions are extremely challenging due to the lack of inexpensive large-scale conformal wearable sensors that are compatible with human activities.

To the extent sensors or the like have been incorporated into textiles, such incorporation results in rigid to semi-rigid garments that are neither as comfortable or as functional as their counterpart garments that are not "smart." The weaving techniques utilized in most instances results in such rigid to semi-rigid garments. Further, to the extent techniques such as embroidery are used to incorporate sensors to form "smart textiles," while they may result in more comfortable and functional textiles, such techniques are not scalable. Thus, these techniques have limited value to possibly no value to companies trying to produce "smart textiles" for any commercial purposes. Despite tremendous progress of wearable electronics benefiting from advanced materials, designs, and manufacturing techniques, automated manufacturing of conformal sensing textiles at whole-body scale with low-cost materials has not been realized yet.

Accordingly, there is a need for wearable sensors that can be mass-produced at a low cost and that can be utilized to enable human activity learning. There is likewise a need to generate data sets from the use of such wearable sensors and to use that data to generate a variety of determinative and/or predictive outcomes, including but not limited to determining present or future actions based on data sensed by wearable sensors. Still further, there is a need to better be able to infer, predict, and/or determine a particular motion or activity based on a limited amount of information or data.

SUMMARY

In accordance with one embodiment of the invention, a system for identifying activity of a subject relative the ground comprises a tactile sensing floor covering for sensing interaction of the subject with the ground and a processing system in communication with the sensor system. The processing system includes at least one processor coupled to a non-transitory memory containing instructions executable by the at least one processor to cause the system to receive an input tactile sequence produced from sensor signals generated by the tactile sensing floor covering sensor system; compare the received input tactile sequence against information in a database that correlates tactile information to particular activities; and identify the activity of the subject based on the comparison.

In various alternative embodiments, the identified activity may include at least one of an identified movement or an identified position of at least one part of the subject. The instructions may further cause the system to trigger a notification based on the identified activity, such as, for example, an alarm, a warning, and/or an indication of an early disease detection. The tactile sensing floor covering may include at least one of a carpet, rug, mat, floor cloth, pad, plank, tile, sheet, or other flooring product. The tactile sensing floor covering may include a piezoresistive pressure sensing matrix fabricated by aligning a network of orthogonal conductive threads as electrodes on each side of a commercial piezoresistive film, wherein each sensor is located at the overlap of orthogonal electrodes. The instructions may further cause the system to implement an encoder that maps the input tactile sequence into a 2D feature map, expands and repeats the 2D feature map to transform the 2D feature map into a 3D feature volume comprising a plurality of voxels, and appends an indexing volume indicating the height of each voxel, and to implement a decoder that runs the appended and indexed 3D feature volume through a set of decoding layers to generate a predicted confidence map for each of a plurality of keypoints, wherein the predicted confidence map is used for comparing the input tactile sequence against information in the database that correlates tactile information to particular activities and identifying the activity of the subject based on the comparison. The processing system may include a neural information processing system. The instructions may further cause the system to collect tactile information for a plurality of test subjects along with reference information and process the collected tactile information and the reference information to produce the information in the database that correlates tactile information to particular activities. The system may include at least one camera, wherein the reference information comprises video or images from the at least one camera of the test subjects producing the collected tactile information.

In accordance with another embodiment of the invention, a method for identifying activity of a subject relative the ground involves receiving, by a processing system, an input tactile sequence produced from sensor signals generated by a tactile sensing floor covering that senses interaction of the subject with the ground; comparing, by the processing system, the received input tactile sequence against information in a database that correlates tactile information to particular activities; and identifying, by the processing system, the activity of the subject based on the comparison.

In various alternative embodiments, the identified activity may include at least one of an identified movement or an identified position of at least one part of the subject. The method may further include triggering, by the processing system, a notification based on the identified activity such as, for example, an alarm, a warning, and/or an indication of an early disease detection. The tactile sensing floor covering may include at least one of a carpet, rug, mat, floor cloth, pad, plank, tile, sheet, or other flooring product. The tactile sensing floor covering may include a piezoresistive pressure sensing matrix fabricated by aligning a network of orthogonal conductive threads as electrodes on each side of a commercial piezoresistive film, wherein each sensor is located at the overlap of orthogonal electrodes. The method may further involve implementing, by the processing system, an encoder that maps the input tactile sequence into a 2D feature map, expands and repeats the 2D feature map to transform the 2D feature map into a 3D feature volume comprising a plurality of voxels, and append an indexing volume indicating the height of each voxel; and implementing, by the processing system, a decoder that runs the appended and indexed 3D feature volume through a set of decoding layers to generate a predicted confidence map for each of a plurality of keypoints, wherein the predicted confidence map is used for comparing the input tactile sequence against information in the database that correlates tactile information to particular activities and identifying the activity of the subject based on the comparison. The processing system may include a neural information processing system. The method may further involve collecting tactile information for a plurality of test subjects along with reference information and processing the collected tactile information and the reference information to produce the information in the database that correlates tactile information to particular activities. The reference information may include video or images of the test subjects producing the collected tactile information.

The present disclosure also provides for a textile-based tactile learning platform that allows researchers to record, monitor, and learn human activities as well as associated interactions with the physical world. The platform can be implemented as a system or method, employing novel, functional (e.g., piezoresistive) fibers that are inexpensive (about US$0.2/m), in conjunction with industrial whole-garment machine knitting, which can be automated, and machine learning workflow, including new calibration and learning algorithms, for example computational pipelines for human-environment interaction recording and learning. The e-scalable manufacturing of this new platform is demonstrated through several non-limiting examples of conformal sensing textiles (over 1000 sensors), e.g., glove, sock, vest, robotic arm sleeve. Further, the disclosed platform can perform weakly supervised sensing correction, endowing strong adaptability to variations in response of individual sensing elements. The present disclosure has resulted in creating a rich dataset (over a million frames) on diverse human-environment interactions, which can be used, by way of non-limiting examples, to classify objects/activities, distinguish environments, predict whole-body poses, discover motion signatures, grasping, and locomotion. The disclosures provided for herein open up new possibilities in wearable electronics, functional textiles, health monitoring, and robot manipulation, among other fields.

One exemplary embodiment of a textile of the present disclosure includes a plurality of functional fibers that are interconnected by loops formed from the plurality of functional fibers such that the plurality of functional fibers forms a knit. The textile also includes a plurality of sensors disposed throughout the textile. The sensors are formed by the plurality of functional fibers.

The functional fibers can include a conductive core and a piezoresistive coating disposed around a circumference of the conductive core. The coating can cover an entire circumference of at least a portion of the conductive core. The conductive core can have many different configurations and be made of a variety of materials. One material can be used to form the core, or a plurality of different materials can be used to form the core. In some embodiments, the conductive core includes stainless steel. Likewise, the piezoresistive coating can have many different configurations and be made of a variety of materials. One material can be used to form the coating, or a plurality of different materials can be used to form the coating. In some embodiments, the piezoresistive coating can include a polydimethylsiloxane elastomer.

The textile can include, or otherwise be, a wearable garment. Some non-limiting examples of wearable garments that can be the textile include a glove, a sock, a top, a bottom, headwear, or a sleeve. Wearable garments are by no means limited to clothes though, as other textiles or garments that can be placed on and/or over an object, human, or animal can also be a wearable garment in the context of the present disclosure. The textile can be flexible.

The plurality of functional fibers can include at least one of automatic inlays or manual inlays and, in some such embodiments, the functional fibers can include a combination of automatic and manual inlays. The plurality of sensors can be configured to adapt to environmental changes and/or can be configured to restore from self-deficit. In some embodiments, the plurality of sensors can be configured to develop a self-supervised sensing pipeline that automatically calibrates a response of the individual sensor.

One exemplary method of manufacturing a textile of the present disclosure includes knitting a plurality of functional fibers together using interconnected loops to form a textile having a plurality of sensors disposed in the textile. The sensors are formed by the plurality of functional fibers. As described herein, and as will be appreciated by a person skilled in the art in view of the present disclosures, the action of knitting is significantly different than the actions of weaving and/or embroidering. The present methods and systems are intended to not use weaving or embroidery techniques in the formation of the whole garments themselves.

In at least some embodiments, the action of knitting a plurality of functional fibers together using interconnected loops can include operating an automated machine to perform the knitting. Knitting a plurality of functional fibers together using interconnected loops can also include digitally knitting the plurality of functional fibers together using interconnected loops. In some embodiments, knitting a plurality of functional fibers together using interconnected loops can include forming at least one of automatic inlays or manual inlays with the plurality of functional fibers. In some such embodiments, the fibers can be formed using a combination of automatic and manual inlays.

The plurality of functional fibers can include a conductive core and a piezoresistive coating. The coating can be disposed around a circumference of the conductive core such that the coating covers an entire circumference of at least a portion of the conductive core. As discussed above, a variety of materials can be used for the conductive core and/or the coating, such materials being able to be used as standalone materials or as a part of a blend or mixture. In some embodiments, the conductive core can include stainless steel and/or the piezoresistive coating can include a polydimethylsiloxane elastomer.

As also discussed above, the textile can include, or otherwise be, a wearable garment. Some non-limiting examples of wearable garments that can be the textile include a glove, a sock, a top, a bottom, headwear, or a sleeve. Wearable garments are by no means limited to clothes though, as other textiles or garments that can be placed on and/or over an object, human, or animal can also be a wearable garment in the context of the present disclosure. The textile can be flexible.

One exemplary system for manufacturing a textile provided for in the present disclosure includes a knitting machine that is configured to knit a plurality of functional fibers together to form a textile using interconnected loops. The knitting machine is configured to operate in an automated manner.

In some embodiments, the system can include a fiber-feeding system. The fiber-feeding system can include a transport system, a coating device, and a curing device. The transport system can be operable to advance a conductive core of a functional fiber of the plurality of functional fibers. The coating device can be configured to apply a piezoresistive coating to the conductive core advanced by the transport system such that the piezoresistive coating covers an entire circumference of at least a portion of the conductive core. The curing device can be configured to cure the piezoresistive coating to the conductive core to form the functional fiber of the plurality of functional fibers.

The knitting machine can be configured to form one or both of automatic inlays or manual inlays with the plurality of functional fibers knitted together using interconnected loops. In some embodiments, the knitting machine is configured to digitally knit the plurality of functional fibers together using interconnected loops.

Similar to other exemplary embodiments described above, the textile formed by the knitting machine can include, or otherwise be, a wearable garment. Some non-limiting examples of wearable garments that can be the textile include a glove, a sock, a top, a bottom, headwear, or a sleeve. Again, wearable garments are by no means limited to clothes though, as other textiles or garments that can be placed on and/or over an object, human, or animal can also be a wearable garment in the context of the present disclosure. Additionally, the textile formed by the knitting machine can be flexible.

One exemplary embodiment of a fiber for use in a textile as provided for in the present disclosure includes a conductive core and a piezoresistive coating. The piezoresistive coating is disposed around a circumference of the conductive core such that the coating covers an entire circumference of at least a portion of the conductive core. As discussed above, a variety of materials can be used for the conductive core and/or the coating, such materials being able to be used as standalone materials or as a part of a blend or mixture. In some embodiments, the conductive core can include stainless steel and/or the piezoresistive coating can include a polydimethylsiloxane elastomer.

The present disclosure also provides for an exemplary method for calibrating sensors associated with a textile. The method includes receiving a plurality of readings from a plurality of sensors associated with a textile that results from an action being performed that yields the plurality of readings. The readings are indicative of one or more parameters used to identify an activity. The method also includes recording the plurality of readings and synchronizing the plurality of readings to calibrate the plurality of sensors.

In some embodiments, the plurality of readings can include readings of at least one of: a pressure, a temperature, a pH level, a chemical level, an electro-magnetic property, an acoustic parameter, or a vibration. Other parameters can also be measured or otherwise read. In instances where the readings are a pressure, performing an action that yields the plurality of readings can include pressing the textile against a digital scale a plurality of times, with the plurality of readings being from each time the textile is pressed against the digital scale. Each sensor of the plurality of sensors can be calibrated individually. Further, each calibration for each sensor can be stored in conjunction with the respective sensor of the plurality of sensors.

One exemplary method of training a neural network in view of the present disclosures includes providing a small sequence of unprocessed tactile responses to a neural network and causing the neural network to output a single frame with the same spatial resolution as the small sequence of unprocessed tactile responses.

The method can also include optimizing the neural network via stochastic gradient descent on a plurality of objective functions. In some embodiments, the method can include increasing a correlation between tactile response and the single frame outputted by the neural network.

A method for identifying an activity, such as a human activity, is another exemplary method provided for in the present disclosure. The method includes receiving tactile information from a smart textile, comparing the tactile information against a database of tactile information that correlates the data to particular activities (e.g., human activities), and identifying the activity based on the comparison.

In some embodiments, the activity is a human activity and it includes various actions related to movement. The identified human activity can include, for example, an identified movement and/or identified position of body parts of a human. The method can also include triggering a notification in view of the identified activity. For example, the notification can include at least one of an alarm, a warning, or an indication of an early disease detection.

The present disclosure also provides for one or more systems that are able to perform one or more of the methods described above or otherwise described herein.

BRIEF DESCRIPTION OF DRAWINGS

The patent or application file contains at least one drawing executed in color. Copies of this patent or patent application publication with color drawing(s) will be provided by the Office upon request and payment of the necessary fee.

Those skilled in the art should more fully appreciate advantages of various embodiments of the invention from the following "Description of Illustrative Embodiments," discussed with reference to the drawings, in which:

FIGS. 12A, 12B, 12C, 12D, and 12E show typical failure cases encountered in the prototype system;

FIG. 13A is a perspective view of exemplary embodiments of coaxial piezoresistive fibers, the fiber being disposed on a roll and incorporated into garments; FIG. 13B is an optical microscope image of each of a stainless steel thread for use in conjunction with a coaxial piezoresistive fiber, a functional fiber, and acrylic yarn; FIG. 13C is a scanning electron microscope (SEM) image of a cross-section as identified in the functional fiber of FIG. 13B; FIG. 13D is an SEM image of the functional fiber of FIG. 13C taken at a closer range; FIG. 13E is an SEM image of the functional fiber of FIG. 13D taken at a closer range and after shear mixing the functional fiber at a high rate of speed; FIG. 13F is a graph illustrating a change in resistance in response to load from a normal force associated with an exemplary embodiment of a sensing wearable of the present disclosure; FIG. 13G is a graph illustrating sensor resistance over time associated with an exemplary embodiment of a sensing wearable of the present disclosure; and FIG. 13H is a graph illustrating sensor resistance in response to load associated with different combination of fabric structures;

FIG. 14A is a schematic illustration of one exemplary embodiment of a method of manufacturing a sensing wearable; FIG. 14B is a top perspective view of one exemplary embodiment of a sensing wearable, as shown a pair of gloves; FIG. 14C is a side perspective view of another exemplary embodiment of a sensing wearable, as shown a sock; FIG. 14D is a side perspective view of yet another exemplary embodiment of a sensing wearable, as shown a vest; FIG. 14E is a side perspective view of still another exemplary embodiment of a sensing wearable, as shown a sleeve for use with a robotic arm; and FIG. 14F is a schematic illustration of various ways by which sensing wearables, such as those illustrated in FIGS. 14B-14E, can used to collect data and learn from the same;

FIG. 15A illustrates tactile information collected from pressing a sensing wearable glove on a digital scale; FIG. 15B illustrates tactile information collected by pressing a sensing wearable glove on a sensing wearable vest; FIG. 15C illustrates both a raw signal image and a self-supervised image that results for each of three different objects when pressed against the sensing wearable glove of FIG. 15A; FIG. 15D illustrates both a raw signal image and a self-supervised image that results for each of three positions when the sensing wearable vest of FIG. 15B contacts an object; FIG. 15E illustrates both a raw signal image and a self-supervised image that results for each of two positions of a foot wearing a sensing wearable sock; and FIG. 15F illustrates both a raw signal image and a self-supervised image that results for each of two positions of a robotic arm wearing a sensing wearable sleeve;

FIG. 16A illustrates example photographs and tactile frames that can assist in the identification of diverse sets of signatures; FIG. 16B illustrates a T-distributed Stochastic Neighbor Embedding (T-SNE) plot from a pose dataset from a sensing wearable vest; FIG. 16C illustrates example photographs and tactile frames of letters pressed on a sensing wearable vest to classify sensory information, such as the letter and orientation; FIG. 16D illustrates a plot of effective input resolution against classification accuracy, as well as a confusion matrix; FIG. 16E is a schematic illustration of a human body illustrating 10 different joint angles that can be predicted by exemplary embodiments of the systems and methods provided for herein; FIG. 16F is a graph illustrating the mean-squared error (MSE) in pose production; FIG. 16G is a graph illustrating the MSE in effective input resolution of a sensor of exemplary embodiments of the systems and methods provided for herein; FIG. 16H is a graph illustrating the MSE in number of input frames (context window) of the systems and methods provided for herein; FIG. 16I provides a comparison of poses predicted by tactile footprint data illustrated in the figure and actual poses associated with the generated tactile footprint data; FIG. 16J provides a comparison of time series predictions of poses from walking predicted by tactile footprint data illustrated in the figure and actual poses from walking associated with the generated tactile footprint data; and FIG. 16K provides principal component analysis (PCA) on tactile maps from walking, with insets therein corresponding to relevant tactile frames from the walking;

FIG. 18 illustrates example photographs and tactile frames of one exemplary embodiment of a sensing sleeve disposed on a robotic arm receiving real-time tactile feedback.

DESCRIPTION OF ILLUSTRATIVE EMBODIMENTS

Figure 1A:
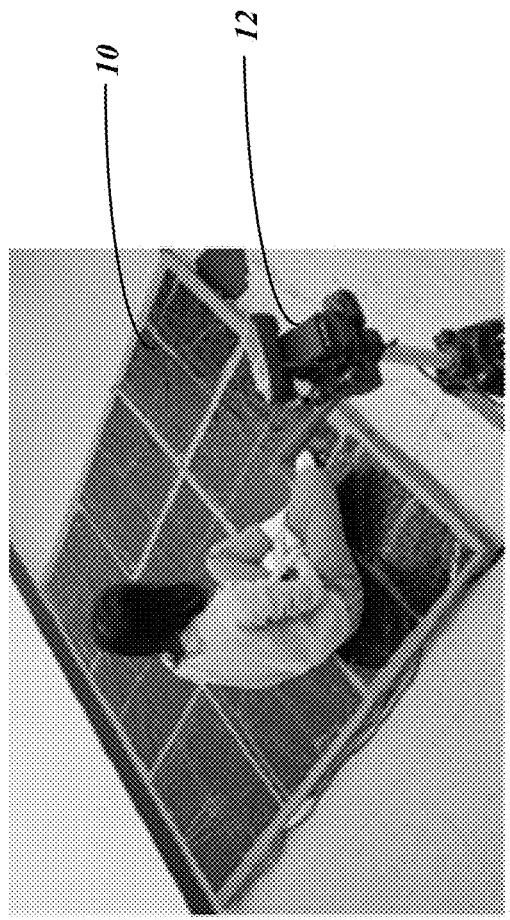
FIG. 1A is a photograph showing a low-cost, high-density, large-scale intelligent carpet system to capture the real-time human-floor tactile interactions, in accordance with certain exemplary embodiments.

Certain exemplary embodiments will now be described to provide an overall understanding of the principles of the structure, function, manufacture, and use of the devices and methods disclosed herein. One or more examples of these embodiments are illustrated in the accompanying drawings. The present disclosure is inclusive of U.S. Provisional Patent Application No. 63/007,675, entitled "SYSTEMS AND METHODS FOR ENABLING HUMAN ACTIVITY LEARNING BY MACHINE-KNITTED, WHOLE-GARMENT SENSING WEARABLES," and filed Apr. 9, 2020, including the Appendices appurtenant thereto, which was incorporated by reference above in its entirety and is referred to herein as "the priority patent application." Any reference to "the present disclosure," "herein," or similar statements is inclusive of the accompanying drawings and the priority patent application including the Appendices, and references to Appendix A, Appendix B, or the Appendices refer specifically to the Appendices in the priority patent application. Applicant expressly reserves the right to amend this patent application to physically incorporate any of the subject matter of the priority patent application, including any figures in the Appendices.

Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Certain exemplary embodiments include systems and methods for estimating 3D poses of a subject from tactile interactions with the ground by recording the interactions with the ground using a tactile sensing floor covering (e.g., in the form of a carpet, rug, mat, floor cloth, pad, plank, tile, flooring product, etc., although it should be noted that such tactile sensing devices are not limited to placement on the floor and instead can be placed on virtually any surface such as walls, doors, furniture, machinery, etc. for sensing subject-to-ground or subject-to-surface interactions, including non-flat surfaces that can be covered by flexible floor coverings or by otherwise altering a floor covering to comply with the contours of the surface) incorporating a sensor system and processing the sensor signals from the incorporated sensor system (which essentially provide a 2D mapping of the interactions with the ground) into estimated 3D poses. Such 3D pose estimation can be useful in a wide range of disciplines including, without limitation, action recognition, gaming, healthcare, and robotics. Also, as opposed to 3D pose estimation using images or video, which can present privacy concerns and also do not perform well in the presence of occlusions, 3D pose estimation based on tactile interactions with the ground can be done more securely and do not suffer from "line of sight" issues. For purposes of this discussion and claims, the term "ground" is used generically to refer to a substantially fixed surface on which the subject is supported such as for standing or walking (e.g., a floor, or perhaps a table or other surface such as for a machine or robot), and terms such as "ground" and "floor" may be used interchangeably.

Aspects are described with reference to an implemented prototype system configured for estimating 3D poses of human subjects based on pressure readings from a tactile sensing floor covering in the form of a carpet incorporating a pressure sensor system (which may be referred to herein for convenience as an "intelligent carpet"), although it should be noted that other forms of tactile sensing floor coverings (e.g., rug, mat, floor cloth, pad, plank, tile, sheet, or other flooring product) incorporating pressure and/or other types of sensors (e.g., temperature, pH, chemical, electromagnetic, electrodermal, acoustic, vibration, etc.) may be used in various alternative embodiments (where, for purposes of this discussion and claims, all such sensors are deemed to provide tactile information when produced due to a subject's physical interaction with the ground). Further, the same or similar systems and methods can be used to estimate position and movement of other subjects that interact with the ground including, without limitation, animals and even non-living subjects such as machinery or robots. Thus, for example and without limitation, a tactile sensing floor covering can be placed on top of another flooring layer (e.g., carpet, rug, or mat on top of an existing floor), under another flooring layer (e.g., a pad under a carpet or rug), or as a top flooring layer (e.g., sensors integrated into flooring planks, tiles, etc.).

The following is a description of the hardware setup for tactile data acquisition, pipeline for ground truth 3D keypoint confidence map generation, as well as data augmentation and synthesis for multi-person pose estimation, in accordance with the prototype system.

FIG. 1A is a photograph showing the data collection setup for the prototype system including a low-cost, high-density, large-scale intelligent carpet 10 to capture the real-time human-floor tactile interactions. Also shown in this figure is a camera 12 used to capture images or video of the subject synchronized with readings from the carpet 10.

Figure 1B:
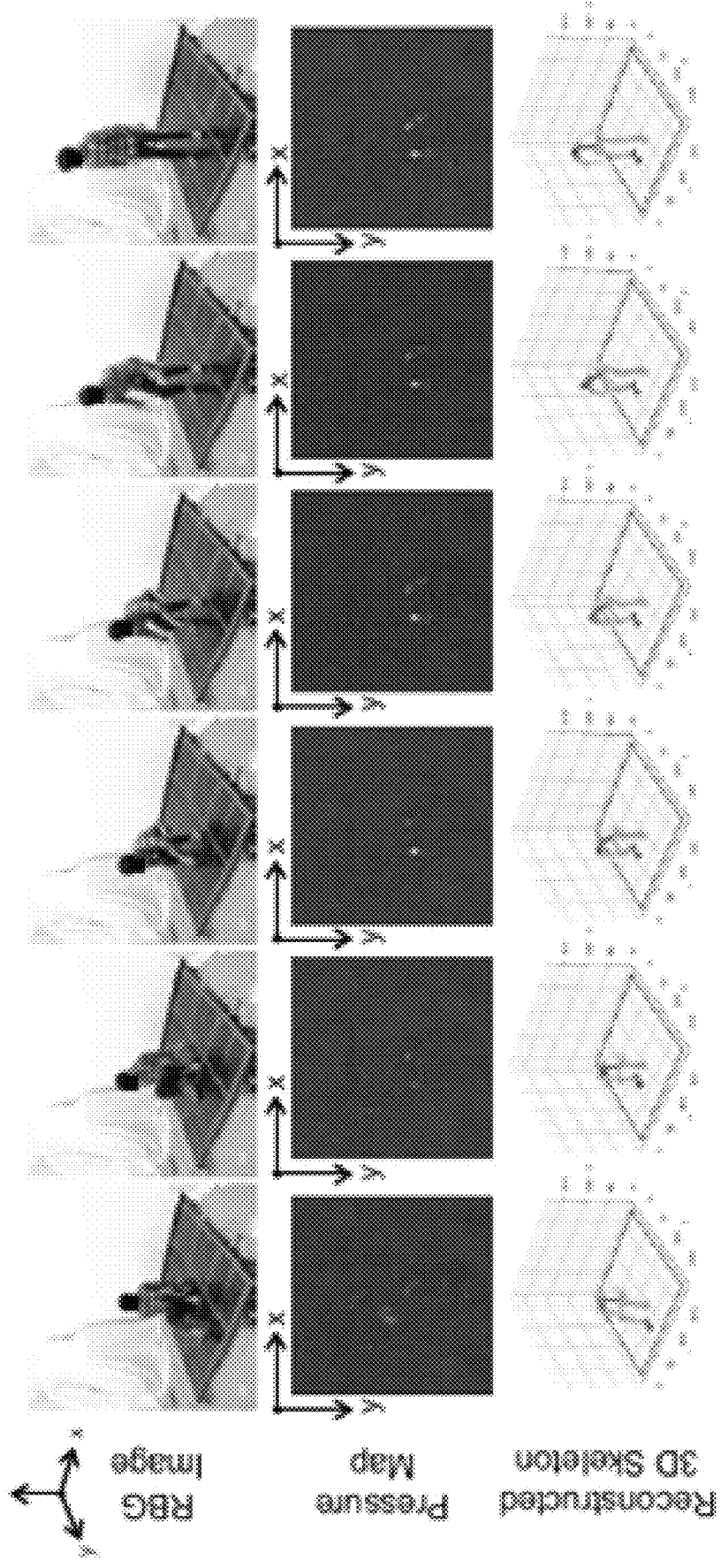
FIG. 1B shows inferred 3D human poses from the captured tactile interactions of a person at various stages when standing up from a sitting position, including, for each stage, an RGB image captured by the camera (top), a pressure map representing signals received from the carpet system (middle), and a reconstructed 3D skeleton produced from the RGB image (bottom), in accordance with certain exemplary embodiments.

FIG. 1B shows inferred 3D human poses from the captured tactile interactions of a person at various stages when standing up from a sitting position, including, for each stage, red green blue (RGB) image captured by the camera (top), a pressure map representing signals received from the carpet system (middle), and a reconstructed 3D skeleton produced from the RGB image (bottom) with different body parts highlighted using different colors (e.g., green for legs, blue for feet, red for torso, etc.), in accordance with certain exemplary embodiments. Each of these will be described in greater detail below.

Figure 2A:
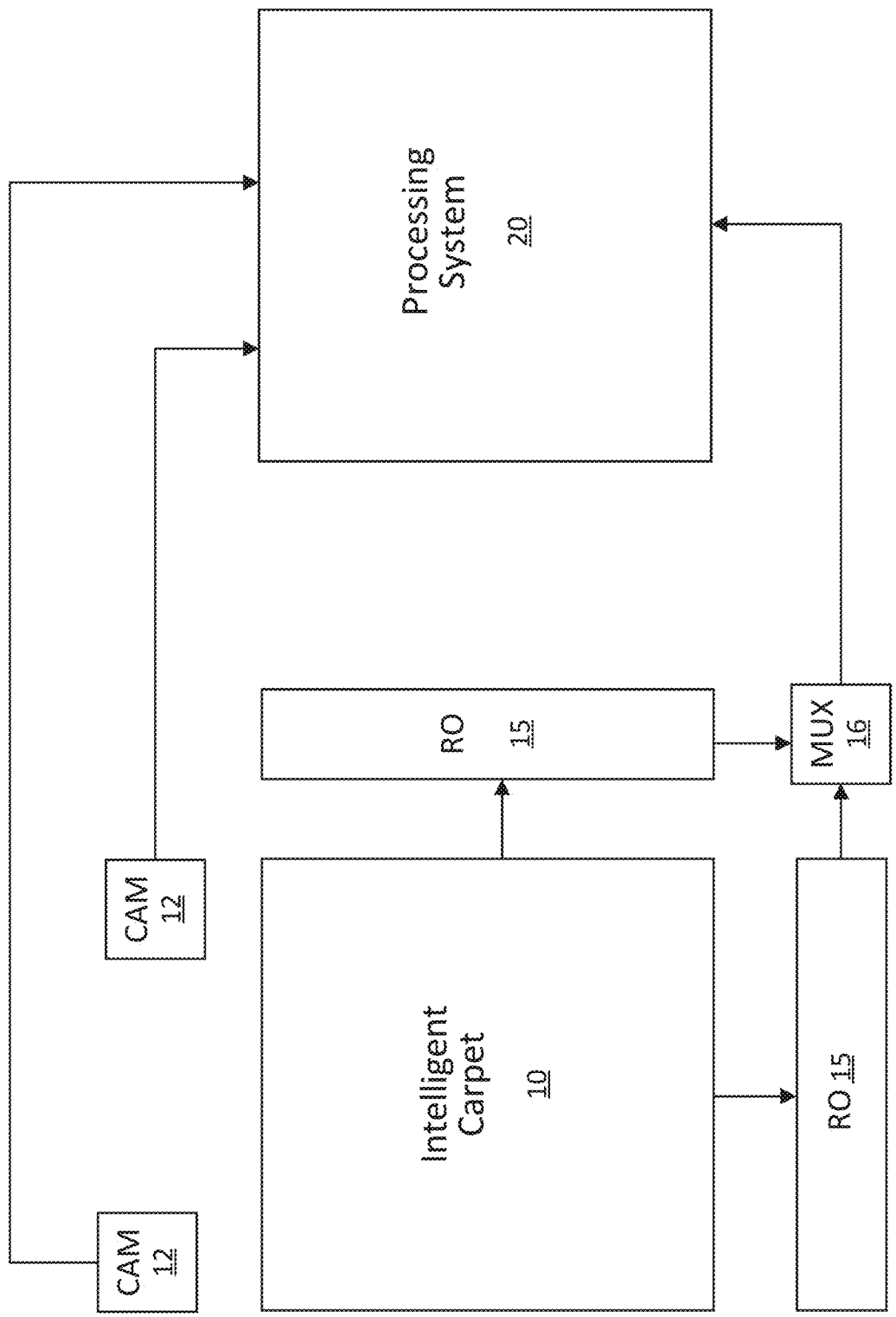
FIG. 2A is a schematic diagram showing relevant components of the tactile data acquisition hardware as used in the prototype system.

FIG. 2A is a schematic diagram showing relevant components of the tactile data acquisition hardware as used in the prototype system including a tactile sensing carpet 10 approximately 6 ft×6 ft square (i.e., spanning around 36 ft$^2$) incorporating 9,216 sensors with a spacing of about 0.375 inches that can be seamlessly embedded on the floor and the corresponding readout (RO) circuits 15 that capture the sensor signals, multiplexing (MUX) circuit 16 that processes the captured sensor signals and provides the processed sensor signals to the processing system 20, and two cameras 12 that enable real-time recordings of high-resolution human-ground tactile interactions for use by a processing system 20 such as a neural information processing system. The tactile sensing carpet 10 of the prototype system was composed of a piezoresistive pressure sensing matrix fabricated by aligning a network of orthogonal conductive threads as electrodes on each side of the commercial piezoresistive films. Each sensor locates at the overlap of orthogonal electrodes and can measure pressure up to about 14 kPa with the highest sensitivity of about 0.3 kPa. This tactile sensing carpet is low-cost (~$100), easy to fabricate, and robust for large-scale data collection. Using the prototype system as depicted in FIG. 2A, the tactile frames with 9,216 individual sensing readouts can be collected, by way of non-limiting example, at a rate of about 14 Hz. With such a large-scale high-resolution tactile sensing platform, the prototype system can not only capture people's foot pressure maps, but also can capture the full tactile interactions between the human and the floor when people are performing complex activities. It should be noted that the configuration of this exemplary tactile sensing carpet can be used to form sensor systems for other embodiments such as wearable sensor systems of the types described below. It also should be noted that tactile sensing floor coverings are not limited to this type of tactile sensing carpet but instead virtually any pressure sensing carpet, rug, or other pressure sensing system can be used in various alternative embodiments. For example, similar tactile sensing carpets can be woven or otherwise produced from coaxial piezoresistive functional fibers of the types discussed below, and exemplary carpets formed from such coaxial piezoresistive functional fibers are discussed below.

With this hardware, over 1,800,000 synchronized tactile and visual frames were collected for 10 different individuals performing a diverse set of daily activities, e.g., lying, walking, and exercising. Employing the visual information as reference, a processing system comprising a deep neural network was implemented to infer the corresponding 3D human pose using only the tactile information. Resulting from this implementation is a database that correlates tactile information to particular human activities such as, for example, standing, sitting, transitioning from sitting to standing or vice versa, movements of the body, or other activities. The processing system then can compare tactile information received from a sensor system to the information in the database in order to identify an activity of the human based on the comparison. For example, the identified activity can include an identified movement or an identified position of at least one body part. The prototype system was found to predict the 3D human pose with average localization error of less than about 10 cm compared with the ground truth pose obtained from the visual information. The learned representations from the pose estimation model, when combined with a simple linear classifier, allowed performance of action classification with an accuracy of about 98.7%. Included below are ablation studies and an evaluation of how well the model generalized to unseen individuals and unseen actions. Moreover, it is shown below that the prototype system can be scaled up for multi-person 3D pose estimation. Leveraging the tactile sensing modality, embodiments open up opportunities for human pose estimation that is unaffected by visual obstructions in a seamless and confidential manner.

Figure 2B:
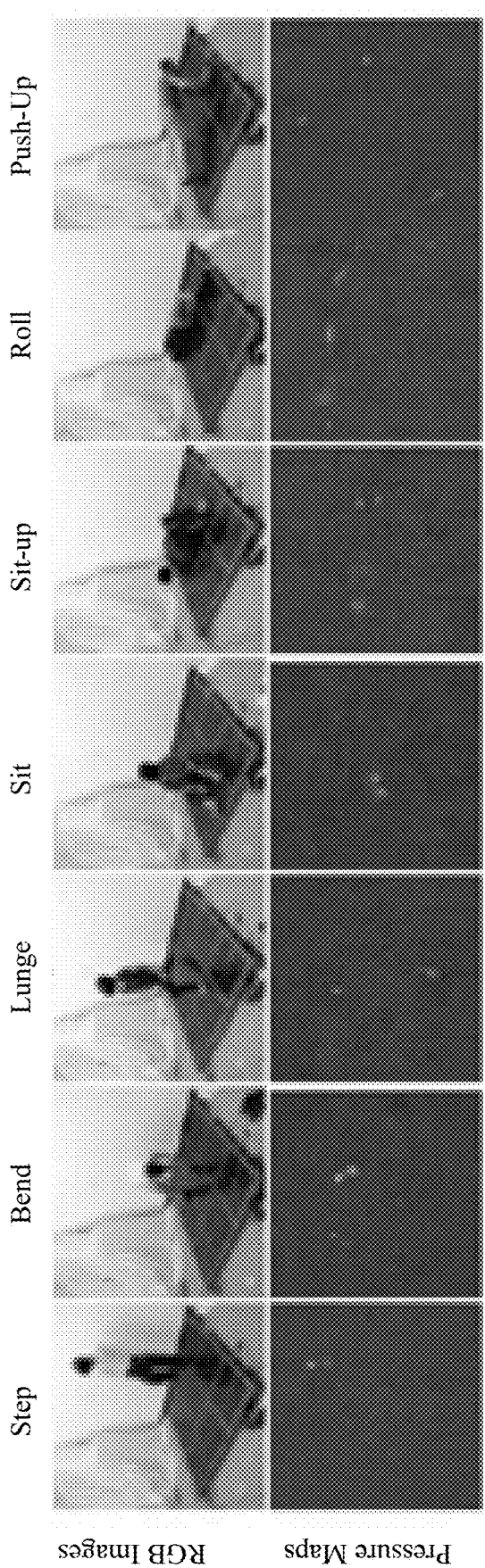
FIG. 2B shows typical pressure maps captured by the carpet from diverse human poses and activities, in accordance with the tactile data acquisition hardware of FIG. 2A.

FIG. 2B shows typical pressure maps captured by the carpet from diverse human poses and activities, in accordance with the tactile data acquisition hardware of FIG. 2A. Specifically, the carpet captures the feet pressure maps when people perform activities in upright positions, as well as the physical contacts between the human body (e.g., hands, limbs) and the floor when people perform exercises and complex actions (e.g., push-ups, sit-ups, and rolling).

The prototype system predicts 3D pose from only the tactile signals, which does not require any visual data and is fundamentally different from past work in computer vision known to the inventors. The introduced tactile carpet has a lower spatial resolution than typical cameras. However, it essentially functions as a type of camera viewing humans from the bottom up. This type of data stream does not suffer from occlusion problems that are typical for camera systems. Furthermore, it provides additional information, such as whether humans are in contact with the ground and the pressure they exert.

The prototype system implements 3D pose label generation as a pipeline to capture and generate the training pairs, i.e., synchronized tactile frames and 3D keypoint confidence maps. The system captures visual data with two cameras that were synchronized and calibrated with respect to the global coordinate of the tactile sensing carpet using standard stereo camera calibration techniques. In order to annotate the ground truth human pose in a scalable manner, the system included a state-of-the-art vision-based system, OpenPose (e.g., Zhe Cao, Tomas Simon, Shih-En Wei, and Yaser Sheikh. Realtime Multi-Person 2D Pose Estimation using Part Affinity Fields. In Proceedings of the IEEE Conference on Computer Vision and Pattern Recognition (CVPR), pages 7291-7299, 2017; Zhe Cao, Gines Hidalgo, Tomas Simon, Shih-En Wei, and Yaser Sheikh. OpenPose: Realtime Multi-Person 2D Pose Estimation using Part Affinity Fields. arXiv preprint arXiv:1812.08008, 2018, each of which is hereby incorporated herein by reference in its entirety), to generate 2D skeletons from the images captured by the cameras.

Figure 3:
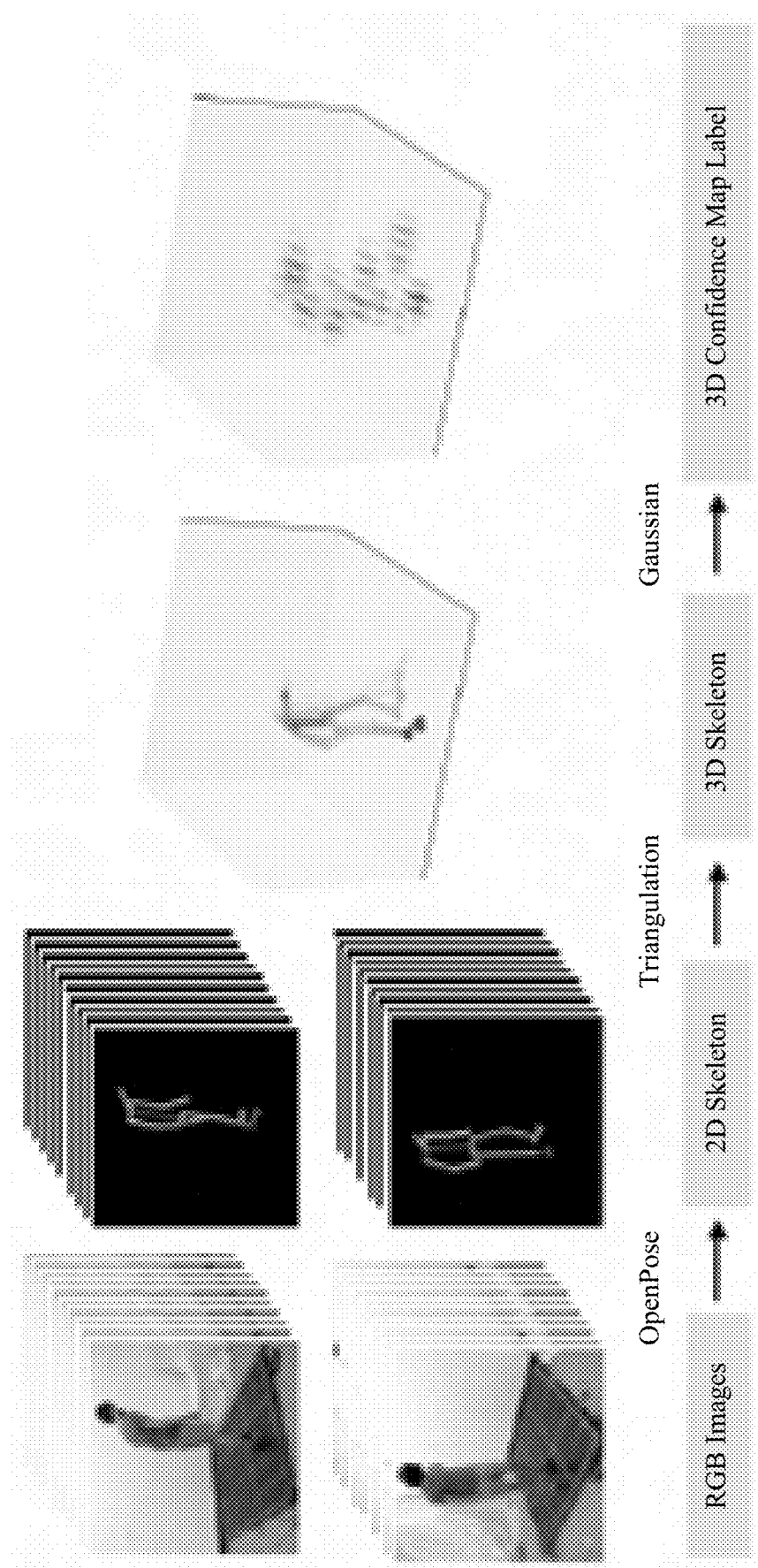
FIG. 3 is a schematic diagram showing 3D keypoint confidence map generation in accordance with the prototype system.

Once the 2D skeletons are generated from the calibrated camera system, the system can triangulate the keypoints to generate the corresponding 3D skeletons. The triangulation results may not be perfect in some frames due to perception noise or misdetection. To resolve this issue, the system can add a post-optimization stage to constrain the length of each link. More specifically, the system can first calculate the length of the links in the skeleton using the median value across the naively triangulated result for each person. For each specific person, the length of the $i^{th}$ link can be denoted as $K_i$. The terms $p^A$ and $p^B$ can then be used to represent the detected N keypoints at a specific time step from the two cameras, which lie in a 2D space, where $p^A = \{p_1^A \ldots p_N^A\}$ and $p_k^A = (x_k^A, y_k^A)$. The system can then calculate the length of each link $\hat{K}_i$ from the naive triangulation result and then can optimize the 3D location of the keypoints p by minimizing the following loss function using stochastic gradient descent:

$$\mathcal{L}^{skeleton} = \sum_{k=1}^{N} \|P^A p_k - p_k^A\| + \sum_{k=1}^{N} \|P^B p_k - p_k^B\| + \sum_{i=1}^{N-1} \|\hat{K}_i - K_i\| \quad (1)$$

where there are N keypoints and N−1 links, $p=\{p_1, \ldots, p_N\}$ lie in 3D space spanned by the world coordinate, $p_k=(x_k, y_k, z_k)$. $P^A$ and $P^B$ are the camera matrices that project the 3D keypoints onto the 2D image frame. N=21 was used in the prototype system. Given the optimized 3D positions of the 21 keypoints on the human skeleton, the system can generate 3D keypoint confidence maps by applying a 3D Gaussian filter over the keypoint locations on a voxelized 3D space. FIG. 3 is a schematic diagram showing 3D keypoint confidence map generation in accordance with the prototype system, where the ground truth voxelized 3D keypoint confidence maps are annotated by first extracting 2D skeleton keypoints from RGB images using OpenPose, and then 3D keypoints can be generated through triangulation and optimization, and finally a 3D Gaussian filter can be applied.

When projecting the human skeletons to the x-y plane (FIG. 1), there is a spatial correspondence between the projection and the tactile signals, which allows for augmenting the dataset by rotating and shifting the tactile frames and the corresponding human skeletons. Due to the restriction of social distancing and the size of the sensing carpet, data collection was conducted with only one person at a time. A multi-person dataset was synthesized by combining multiple single-person clips. In other words, the synchronized tactile frames and the generated 3D keypoint confidence maps were added up from different recording clips. For the sake of the prototype system, it was assumed that people rarely perform actions with one on top of the other, so it was assumed that the pressure maps induced by the actions of different people will not overlap at any given time. Therefore, the location of each person was specified by creating anchor boxes of the human skeleton projected onto the floor plane, and then frames with the Intersection over Union (IoU) larger than 0.1 were removed to ensure that the skeletons and tactile signals from different people did not overlap with each other. The training of the models was entirely based on the single-person dataset and the synthetic multi-person variants. Synchronized visual and tactile data were recorded for multiple people but only for evaluation purposes.

The following presents details of the pose estimation model in accordance with the prototype system including how the tactile frames were transformed into 3D volumes indicating the confidence map of the keypoints and how it was extended to multi-person scenarios. Implementation details are also presented.

Figure 4:
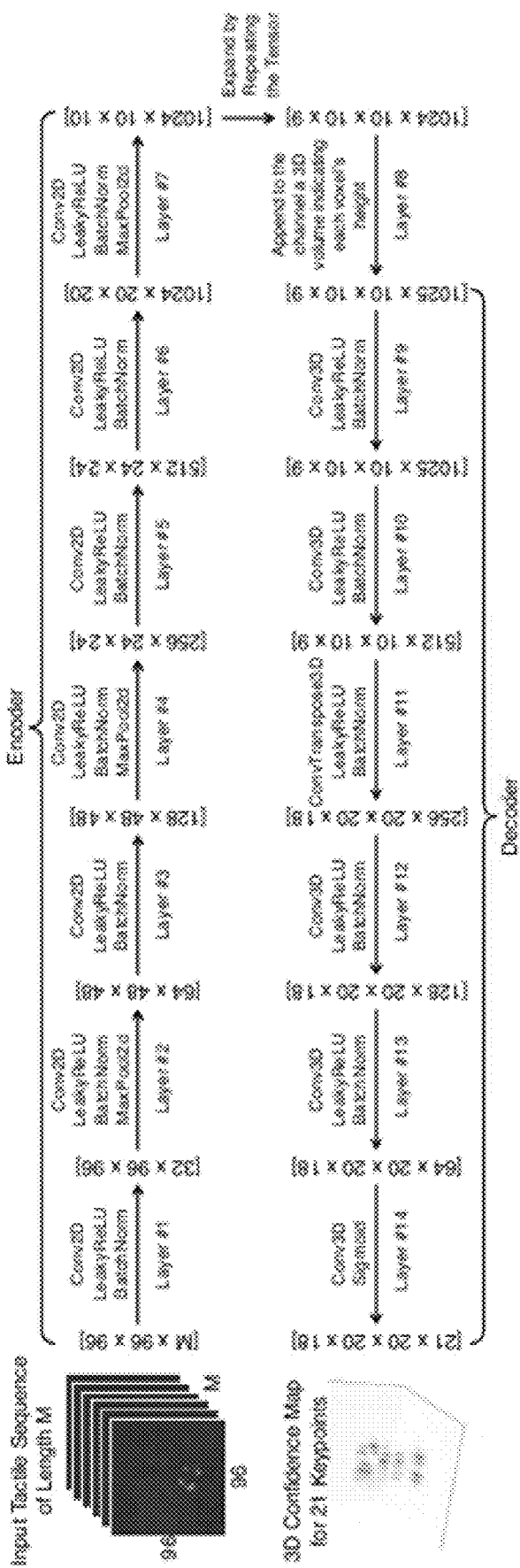
FIG. 4 is a schematic diagram showing an overview of the model for 3D human pose estimation.

For keypoint detection using tactile signals, the goal of the model is to take the tactile frames as input and predict the corresponding 3D human pose. The ground truth human pose estimated from the multi-camera setup is used as the supervision and to train the model to predict the 3D confidence map of each of 21 keypoints, including head (nose), neck, shoulders, elbows, waists, hips (left, right and middle), knees, ankles, heels, small toes, and big toes. To include more contextual information and reduce the effects caused by the sensing noise, instead of taking a single tactile frame as input, the model takes a sequence of tactile frames spanning a temporary window of length M as input (FIG. 4). For each input segment, the model can process the spatiotemporal tactile information and output the keypoint confidence maps in 3D that correspond to the middle frame. As shown in FIG. 1, the input tactile frames lie in 2D space, which has good spatial correspondence with the human skeleton over the x-y plane (the floor plane). The model can build on top of a fully convolutional neural network to exploit such spatial equivariance. The encoder of the model can use 2D convolution to process the tactile frames. Then, to regress the keypoints in 3D, the feature map can be expanded by repeating it along a new dimension in the middle of the network (FIG. 4), which essentially transforms the 2D feature map into a 3D feature volume. However, naive 2D to 3D expanding via repetition can introduce ambiguities as subsequent convolutional layers use shared kernels to process the feature, particularly because it can be difficult or impossible to determine the height of a specific voxel, making it hard to regress the keypoint location along the z-axis. To resolve this issue, a new channel can be added to the 3D feature map with a 3-dimensional indexing volume, indicating the height of each voxel. Then, 3D convolution can be used to process the feature and predict the 3D keypoint confidence map for each of the 21 keypoints. The detailed architecture and the size of the feature maps along the forwarding pass are shown in FIG. 4. The model can be optimized, for example, by minimizing the Mean Squared Error (MSE) between the predicted keypoint heatmap and the ground truth using, for example, an Adam optimizer (e.g., Diederik P Kingma and Jimmy Ba. Adam: A method for stochastic optimization. arXiv preprint arXiv:1412.6980, 2014, which is hereby incorporated herein by reference in its entirety). Spatial softmax can be used to transform the heatmap into the keypoint location and to include an additional loss term $\mathcal{L}^{link}$ to constrain the length of each link in the skeleton to lie in the range of normal human limb length. For each data point, the loss function can be defined as:

$$\mathcal{L} = \frac{1}{N}\sum_{i=1}^{N} \|H_i - \hat{H}_i\| + \frac{1}{N-1}\sum_{i=1}^{N-1} \mathcal{L}_i^{link}, \quad (2)$$

where N denotes the number of keypoints, N−1 is the number of links in the skeleton, $H_i$ and $\hat{H}_i$ represent the ground truth and the predicted 3D keypoint confidence maps. The link loss can be defined as follows:

$$\mathcal{L}_i^{link} = \begin{cases} K_i^{min} - \hat{K}_i, & \text{if } \hat{K}_i < K_i^{min}. \\ \hat{K}_i - K_i^{max}, & \text{if } \hat{K}_i > K_i^{max}. \\ 0, & \text{otherwise,} \end{cases} \quad (3)$$

where $\hat{K}_i$ is the link length calculated from the prediction, $K_i^{min}$ and $K_i^{max}$ represent the 3$^{rd}$ and 97$^{th}$ percentile of each of the body limb length in the training dataset.

When moving into multi-person scenarios, each keypoint confidence map can contain multiple regions with high confidence that belong to different people. Therefore, the system can threshold the keypoint confidence map to segment out each of these high confidence regions, and then can calculate the centroid of each region to transform it into the 3D keypoint location. To associate the keypoints that belong to the same person, the system can start from the keypoint of the head and traverse through the person's skeleton (represented as a tree) to include the remaining keypoints. Every time the system wants to add a new keypoint to the person, e.g., the neck, the system can select the one among multiple extracted keypoint candidates with the closest L2 distance to its parent, e.g., head, which can have already been added to the person on the skeleton tree. This method works well when people are kept at a certain distance from each other, as well as possibly in other contexts. The inventors contemplate implementing more complicated and effective techniques to handle cases where people are very close to each other but were unable to do so at the time of invention due to certain medical protocol issues (i.e., COVID-19 related).

The prototype system can be implemented using PyTorch (e.g., Adam Paszke, Sam Gross, Francisco Massa, Adam Lerer, James Bradbury, Gregory Chanan, Trevor Killeen, Zeming Lin, Natalia Gimelshein, Luca Antiga, et al. Pytorch: An imperative style, high-performance deep learning library. In Advances in neural information processing systems, pages 8026-8037, 2019, which is hereby incorporated herein by reference in its entirety). The model includes an encoder and a decoder. The encoder can map the input tactile sequence into, for example, a 10×10 feature through 7 blocks of Conv2D-LeakyReLU-BatchNorm and then can expand and repeat the feature along the last dimension to transform the 2D feature map into a 3D feature volume. After appending an indexing volume indicating the height of each voxel, the system can run the feature through a set of decoding layers to generate the predicted confidence map for each keypoint. In the prototype system, the model can be trained by minimizing Eq. 2 using a learning rate of 1e-4 and a batch size of 32. FIG. 4 includes a schematic diagram showing an overview of the model for 3D human pose estimation. As shown in FIG. 4, the encoding part of the network can include seven (7) groups of layers. The Conv2D in the first five (5) and the $7^{th}$ layers use 3×3 kernels and 1×1 padding. The $6^{th}$ uses 5×5 kernels and zero padding. As shown, a 2×2 MaxPool2D can also be applied in the $2^{nd}$, $4^{th}$, and $7^{th}$ layers to reduce the resolution of the feature maps. The tactile feature maps can be expanded to 3D, for example, by repeating the tensor nine (9) times along the last dimension, and then appending the channel with a 3D indexing volume indicating the height of each voxel. The decoding network can take in the resulting tensor and predict the 3D confidence maps of the keypoints. The decoder can include, for example, five (5) layers of 3×3×3 3D convolution with a padding of 1×1×1. The $11^{th}$ layer can use, for example, a kernel size of 2×2×2 with a stride of two (2) to increase the resolution. Batch normalization and leaky rectified linear unit (ReLU) can be applied after each layer, although in the illustrated embodiment, it is not applied after the last one, where instead a Sigmoid activation function is used to regress the confidence value.

Figure 5:
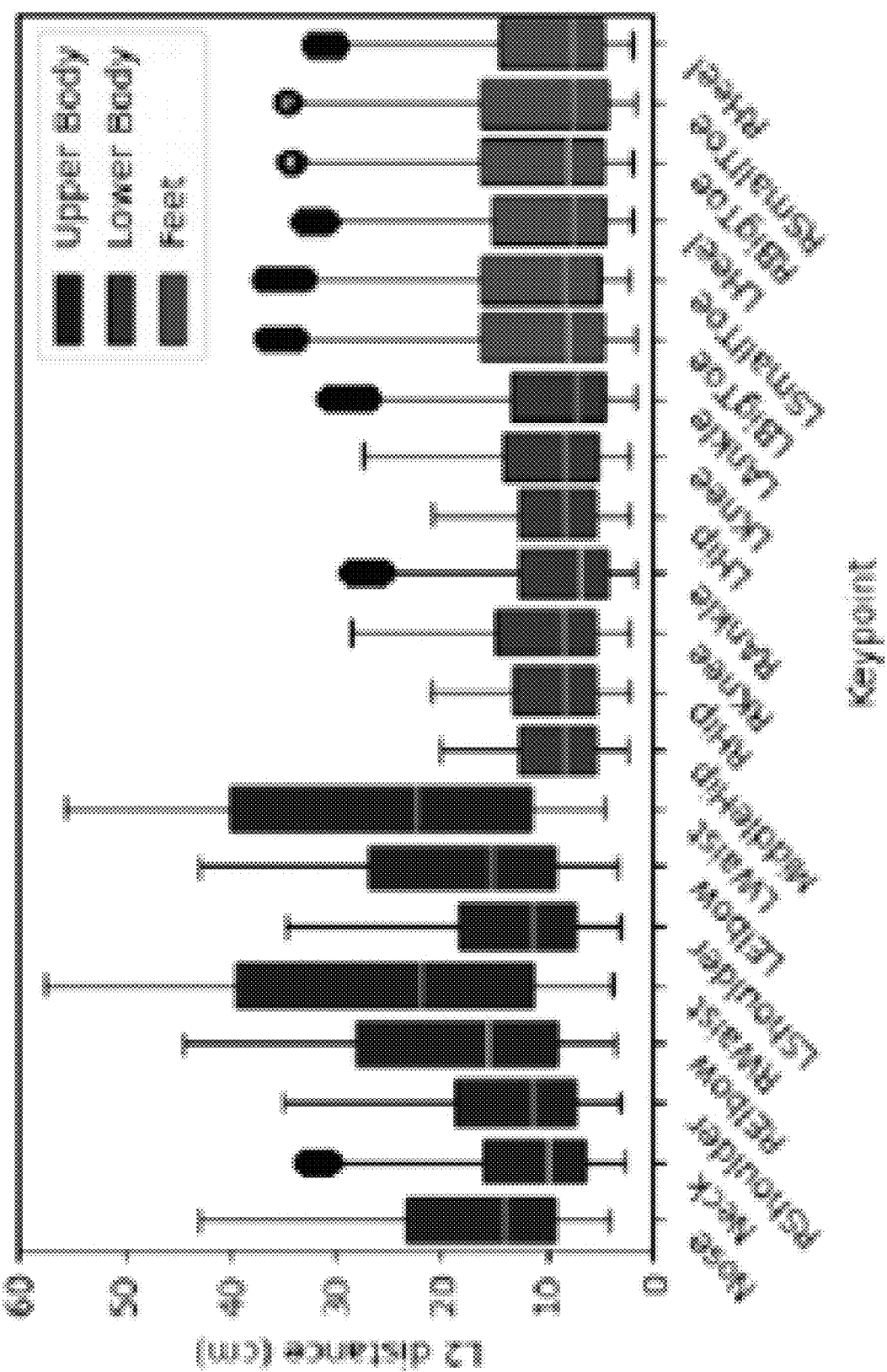
FIG. 5 shows Euclidean (L2) distance between the predicted single-person 3D skeleton (21 keypoints) and the ground truth label.

In accordance with the present disclosure, single-person pose estimation was trained with 135,000 pairs of tactile and visual frames and validated on 30,000 pairs of frames. Performance was tested on a held-out test set with 30,000 tactile frames. Euclidean distance (L2) was used as the evaluation metric to compare the predicted 3D human pose to the corresponding ground truth human pose retrieved from the visual data. FIG. 5 shows the Euclidean (L2) distance between the predicted single-person 3D skeleton (21 keypoints) and the ground truth label, i.e., the Euclidean (L2) distance of each keypoint and the localization error of each body part. The following table shows the average keypoint localization error of body parts along the X, Y, and Z axis in the real-world coordinate:

| Axis | Ave. | Head | Shoulder | Elbow | Waist | Hip | Knee | Ankle | Feet |
|---|---|---|---|---|---|---|---|---|---|
| X | 6.8 | 6.4 | 6.3 | 8.9 | 10.9 | 4.6 | 5.8 | 5.6 | 6.4 |
| Y | 7.2 | 8.0 | 6.5 | 8.8 | 10.9 | 5.2 | 5.8 | 5.7 | 6.7 |
| Z | 6.8 | 9.6 | 7.0 | 8.9 | 14.4 | 4.0 | 4.0 | 3.1 | 3.5 |

As shown, since the changes in pressure maps are dominated by the positions and movements of the lower body and the torso, their predictions are more accurate. Thus, generally, keypoints on the lower body (e.g., knee and ankle) and the torso (e.g., shoulder and hip) hold higher accuracy compared with the keypoints on the upper body (e.g., waist and head). Further, the model can obtain better predictions if the keypoints are closer to the torso on the skeleton tree—the prediction error increases as the keypoints move further away from the torso, e.g., shoulders to elbows, and then to the waist.

Figure 6A:
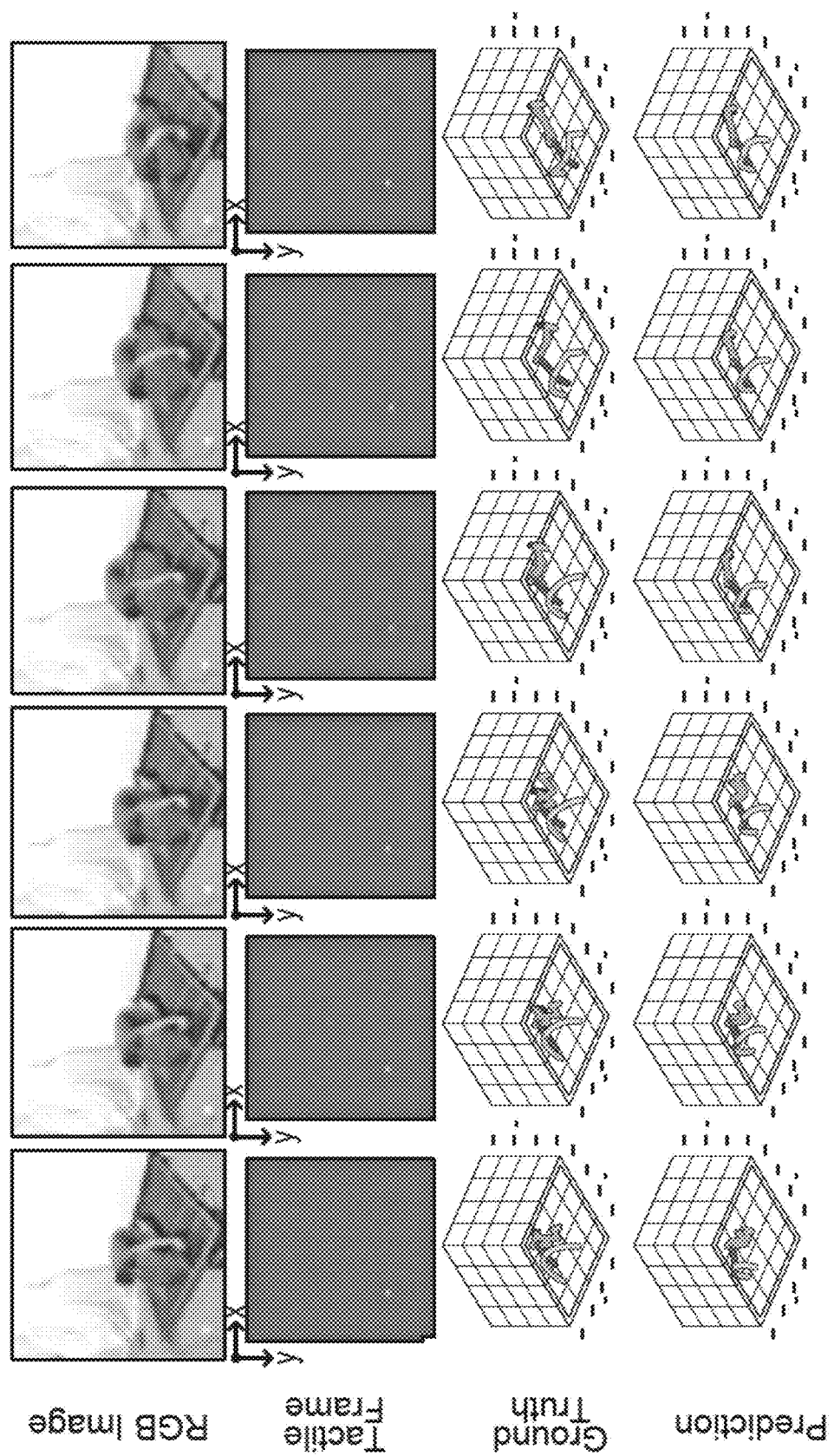
FIGS. 6A-6D show some qualitative results of single-person 3D human pose estimations across time steps.
Figure 6B:
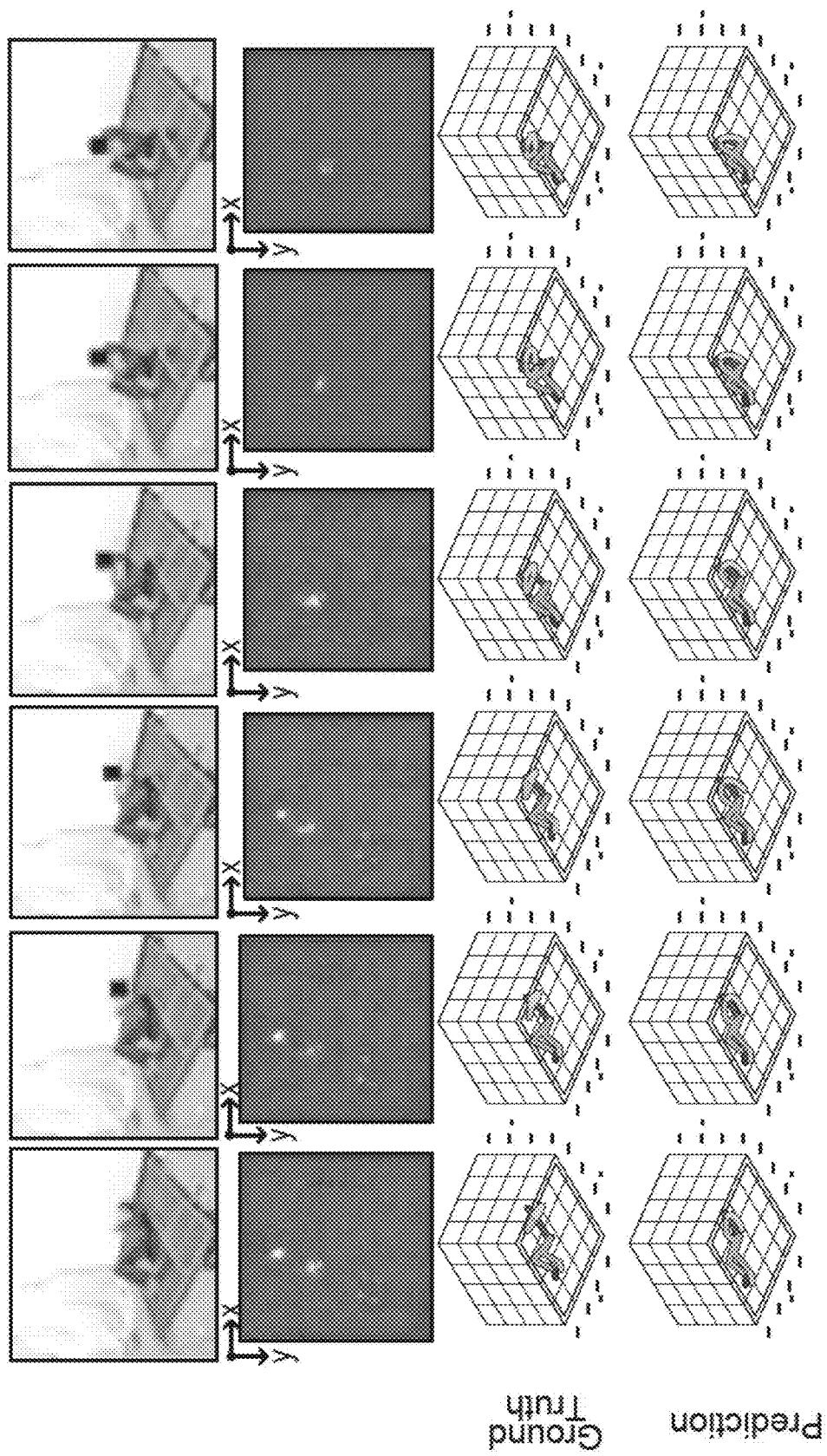
Figure 6C:
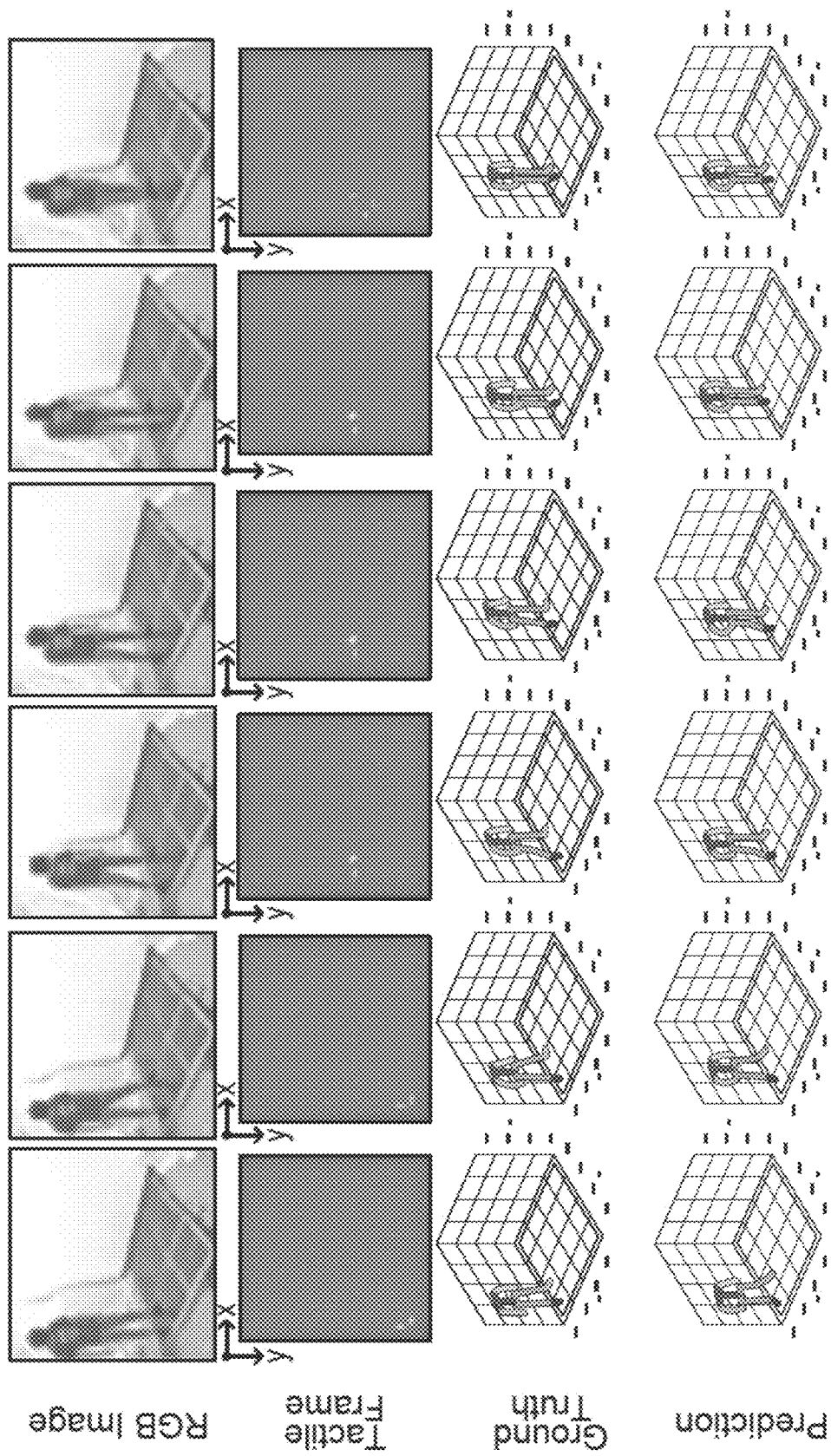
Figure 6D:
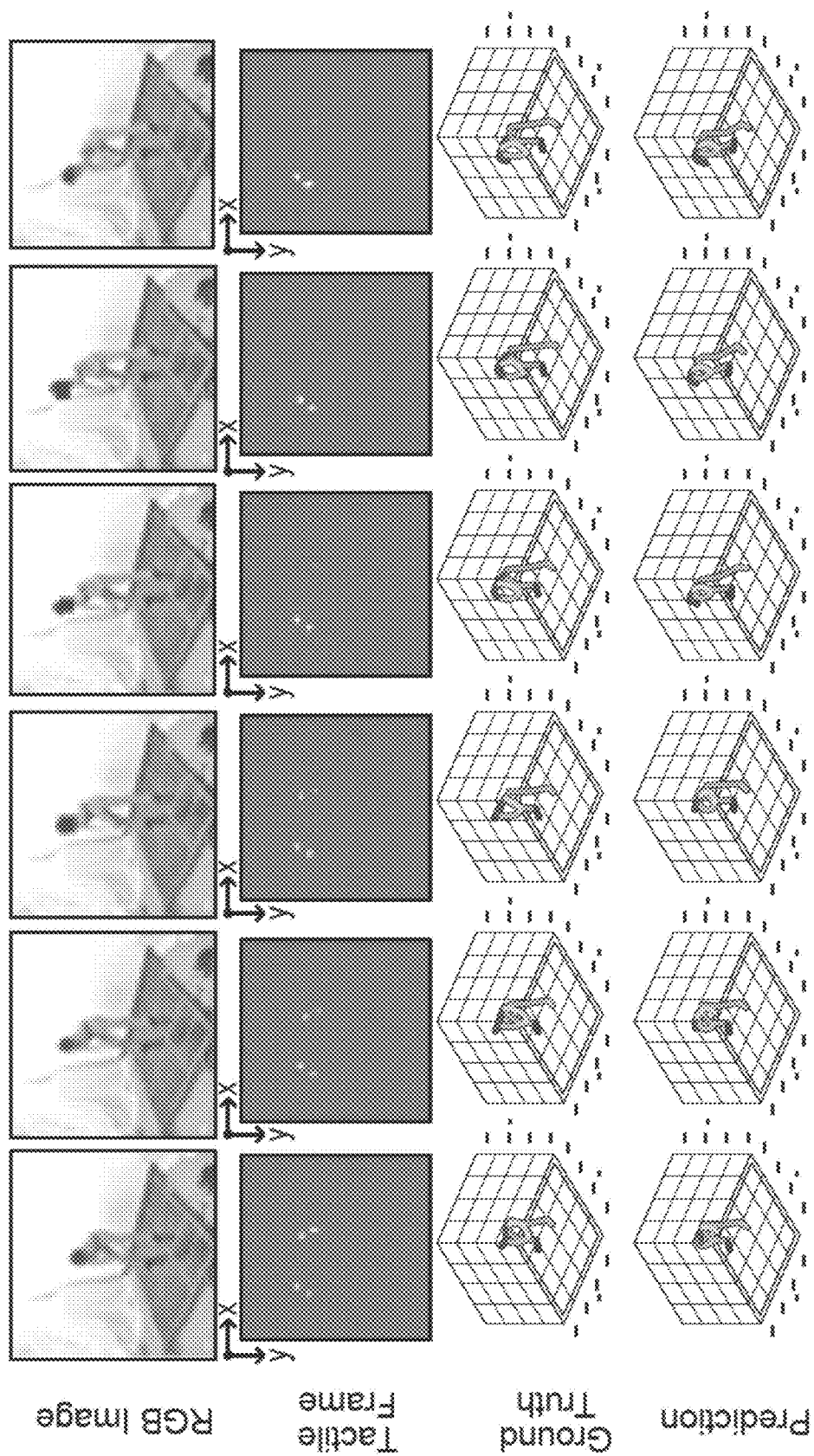
Figure 7:
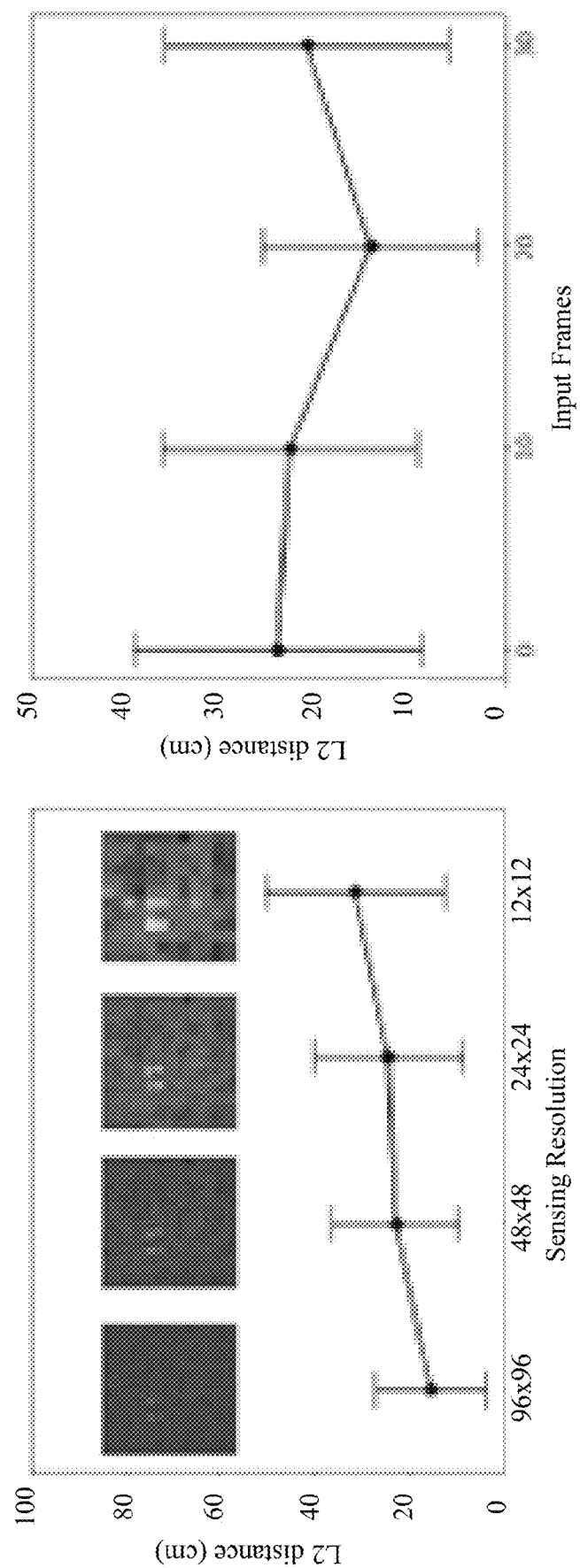
FIG. 7 shows model performance with different sensing resolutions and number of input frames.

FIGS. 6A-6D show some qualitative results of single-person 3D human pose estimations across time steps, including, for each sequence, from top to bottom, the RGB image as ground truth annotation (only used here for visualization purpose), the captured tactile frame, the ground truth 3D skeleton, and the predicted 3D skeleton from the model using only the tactile frames (unit: cm). FIG. 6A depicts a person performing a push-up. FIG. 6B depicts a person performing a sit-up. FIG. 6C depicts a person making mainly head movements. FIG. 6D depicts a person making certain body movements. The predicted poses are consistent over time with a smooth transition along the corresponding trajectories. Ablation studies were performed on the sensing resolution of the intelligent carpet. To ablate the tactile sensing resolution, the value in each 2×2 grid was reassigned with the average of the four values, which reduces the effective resolution from 96×96 to 48×48, and then used the same training pipeline to derive the predictions. A similar procedure was employed for evaluating model performance with effective sensing resolutions of 24×24 and 12×12. FIG. 7 shows model performance with different sensing resolutions (left) and number of input frames (right). As FIG. 7 illustrates, the prediction accuracy decreases with the decrease of sensing resolution, which highlights the importance of a high density, large-scale tactile sensing platform. Based on an ablation study on the number of input frames, the best performance in this model was obtained with 20 input frames (~1.5 sec).

Figure 8A:
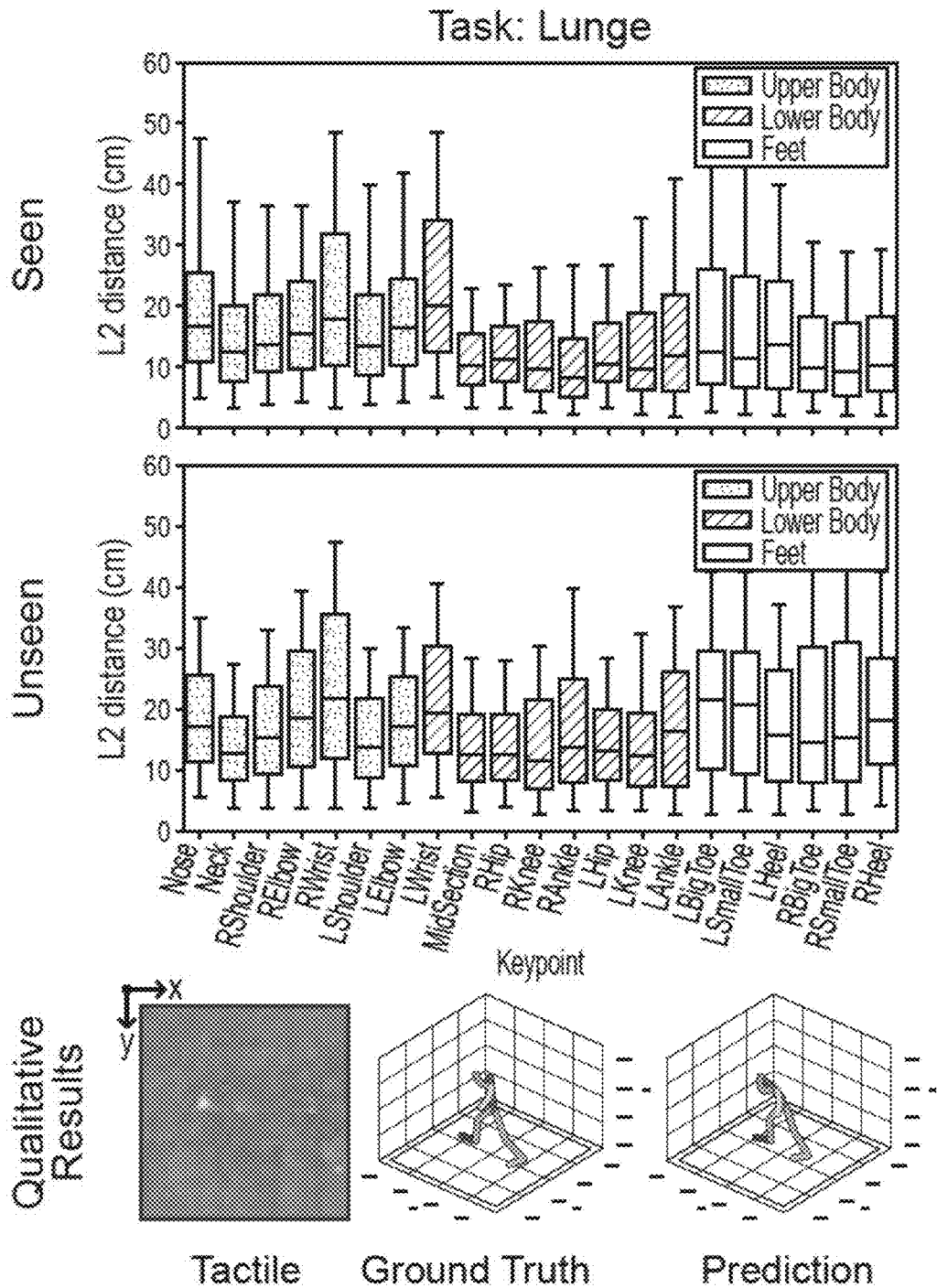
FIGS. 8A-8C show generalization results including localization error of predictions on seen tasks and individuals where the training was performed on the full dataset including all tasks and individuals (top), localization error of predictions on unseen tasks and individuals where the training was performed on a split dataset excluding specific actions and individuals (middle) and qualitative results on unseen tasks and individuals (bottom) for three tasks, specifically a lunge (FIG. 8A), a push-up (FIG. 8B), and a sit-up (FIG. 8C)
Figure 8B:
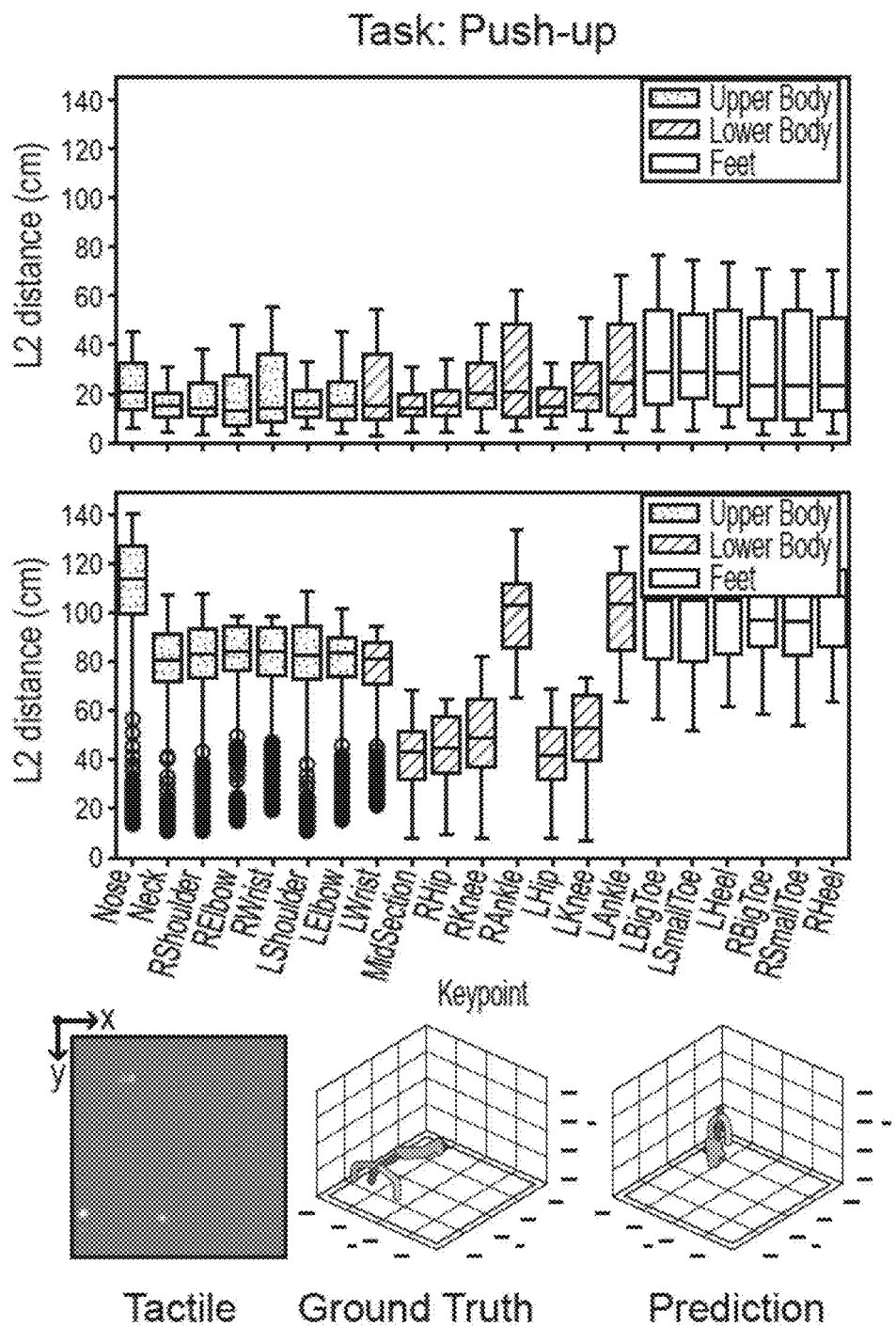
Figure 8C:
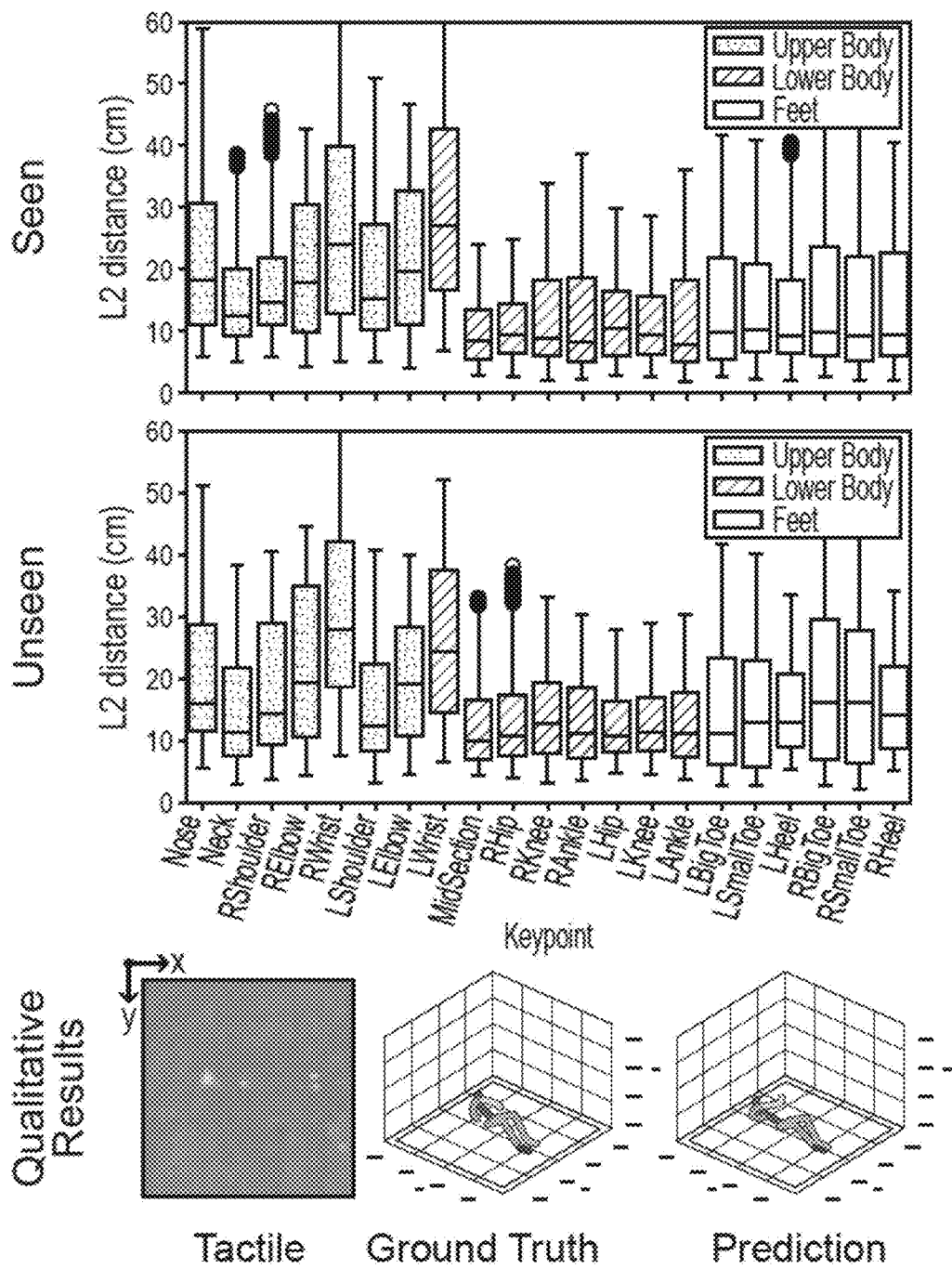

Also, an evaluation of how well the model generalizes to unseen individuals and activities was conducted. FIGS. 8A-8C show generalization results including localization error of predictions on seen tasks and individuals where the training was performed on the full dataset including all tasks and individuals (top), localization error of predictions on unseen tasks and individuals where the training was performed on a split dataset excluding specific actions and individuals (middle) and qualitative results on unseen tasks and individuals (bottom) for three tasks, specifically a lunge (FIG. 8A), a push-up (FIG. 8B), and a sit-up (FIG. 8C). As demonstrated in these figures, the model generalizes to unseen people with a negligible increase of the keypoint localization error but has varying performance on different types of unseen tasks. For example, as shown in FIGS. 8A and 8C, the learned model easily generalizes to poses with pressure maps similar to the pressure maps on which the model was trained. However, as shown in FIG. 8B, the learned model delivers a less accurate performance with tactile imprints that the model has never encountered. In this instance, the model failed to predict the push-up pose, which induces pressure imprints that are vastly different from the training distribution, and instead generalized to the lunging pose, where the pressure maps are mainly directed by the human's center of mass. When deploying the system more generally, it is understood that a more systematic data collection procedure covering more typical human activities will be needed to achieve a more reliable pose estimation performance. More accurate predictions, nevertheless, can be achieved once additional data is collected in view of the present disclosures, and thus extending the present disclosures to other poses is within the scope of the present disclosure. A person skilled in the art will understand many other poses that can be predicted in view of the present disclosures.

To obtain a deeper understanding of the learned features in the pose estimation network, action classification can be performed by applying a linear classifier on the downsampled tactile feature maps. In the studies associated with the present disclosures, this was done using the dataset on one single person performing 10 different actions, where 80% was used for training, 10% for validation, and 10% for testing.

Figure 9:
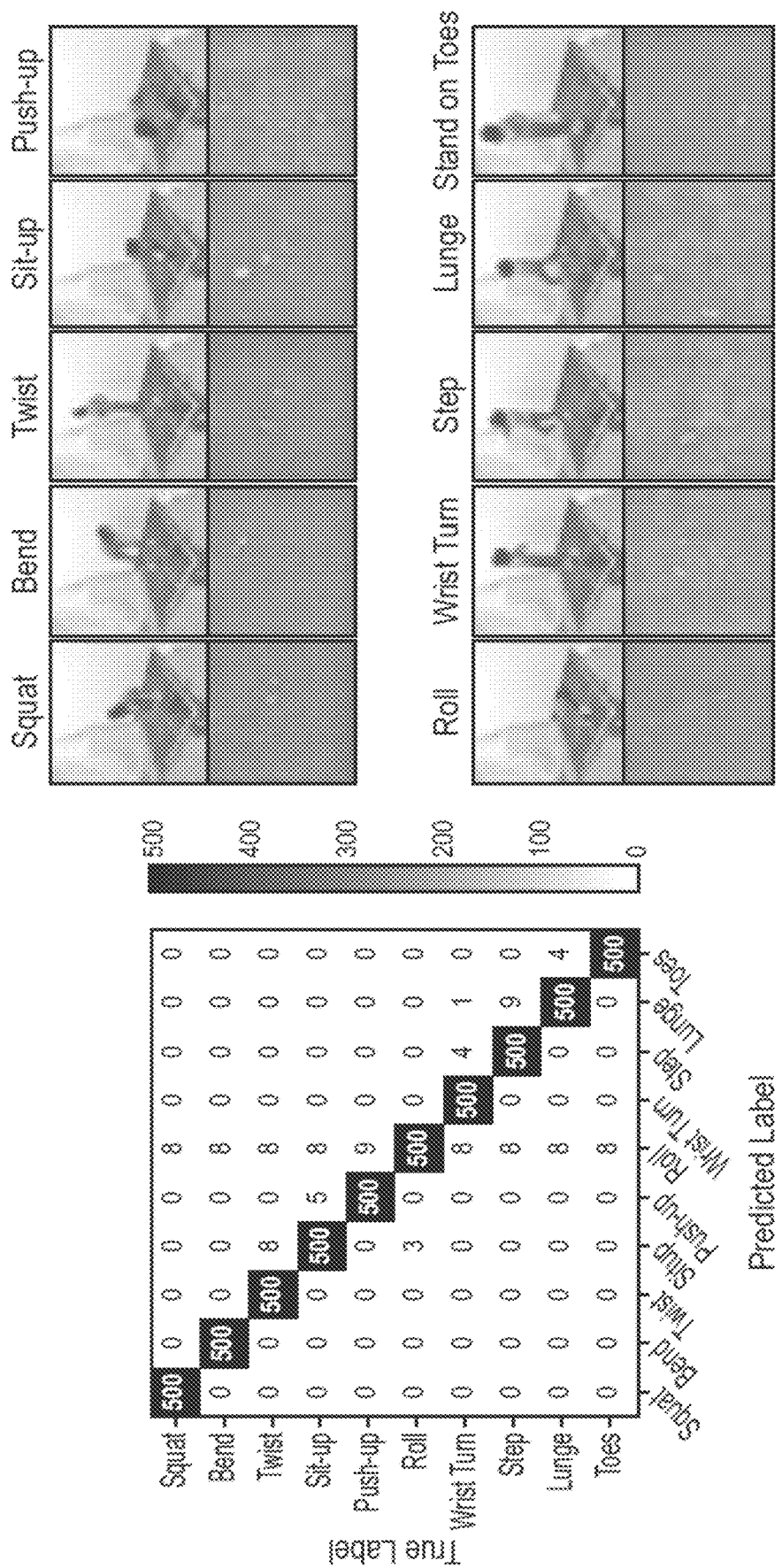
FIG. 9 shows results on action classification including a confusion matrix of action classification using a linear classifier on the learned features from the pose estimation model and representative tactile frames from different actions.

FIG. 9 shows results on action classification including a confusion matrix of action classification using a linear classifier on the learned features from the pose estimation model (left) and representative tactile frames from different actions (right). As demonstrated in FIG. 9, the prototype system obtained an accuracy of about 97.8%, suggesting that the learned features contain semantically meaningful information on the input tactile frames and demonstrating the capability of the model to facilitate downstream classification tasks.

Figure 10:
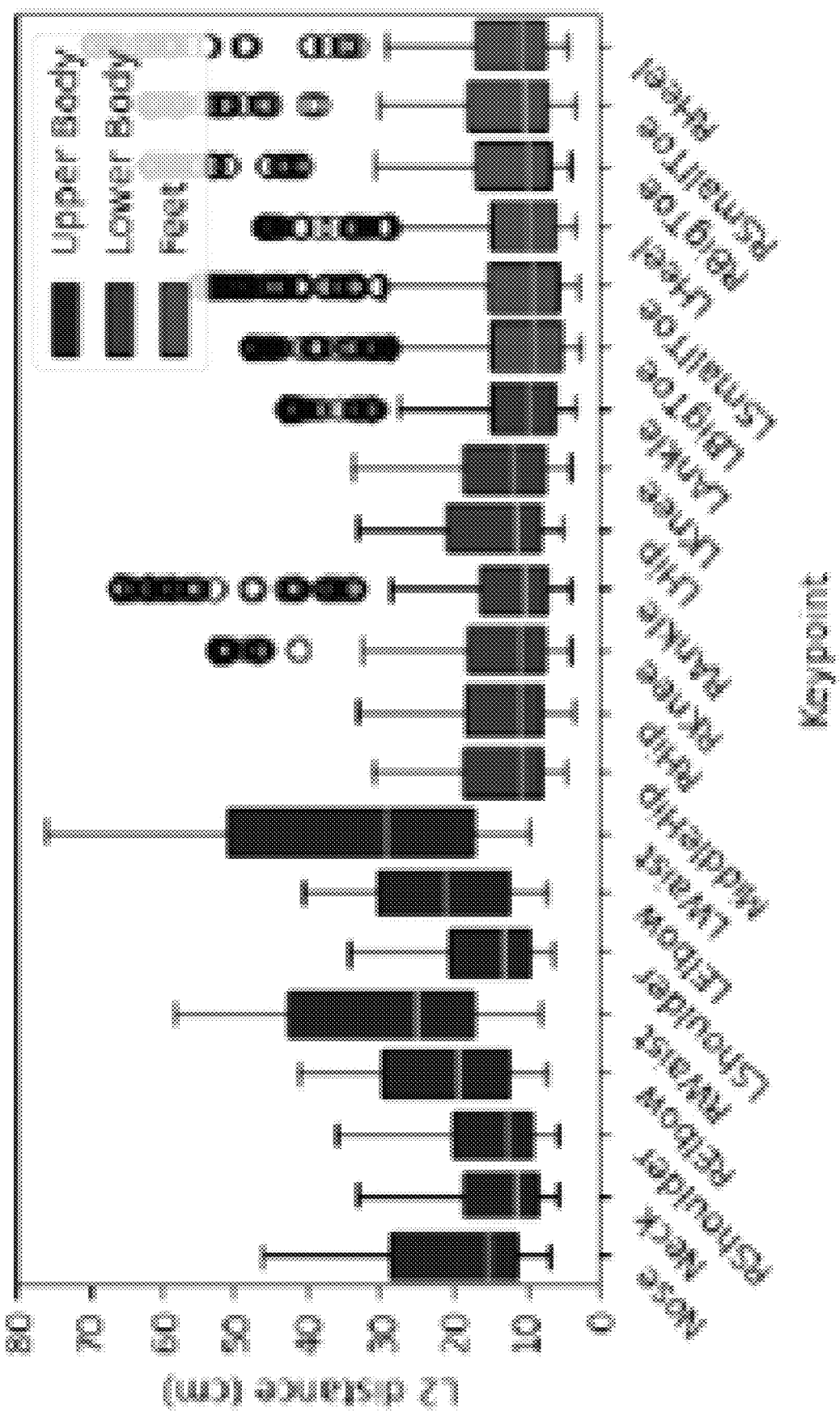
FIG. 10 shows results on multi-person scenarios including Euclidean distance between the predicted multi-person 3D skeleton and the ground truth.

The model was extended for multi-person pose estimation. As discussed above, the multi-person pose estimation model was trained and validated with 112,000 and 10,000 pairs of synthesized tactile frames and keypoint confidence maps. Performance was evaluated with 4,000 recorded tactile frames of two people performing stepping, sitting, lunging, twisting, bending, squatting, and standing on toes. FIG. 10 shows results on multi-person scenarios including Euclidean distance between the predicted multi-person 3D skeleton and the ground truth. The following table shows the average keypoint localization error of body parts along the X, Y, and Z axis in the real-world coordinate:

| Axis | Ave. | Head | Shoulder | Elbow | Waist | Hip | Knee | Ankle | Feet |
|---|---|---|---|---|---|---|---|---|---|
| X | 14.5 | 14.1 | 10.1 | 15.3 | 24.7 | 10.2 | 12.6 | 14.1 | 14.9 |
| Y | 12.9 | 13.9 | 10.8 | 15.9 | 21.6 | 10.1 | 11.0 | 9.7 | 9.9 |
| Z | 12.7 | 16.6 | 13.2 | 17.3 | 23.9 | 10.0 | 8.0 | 6.5 | 6.4 |

Figure 11A:
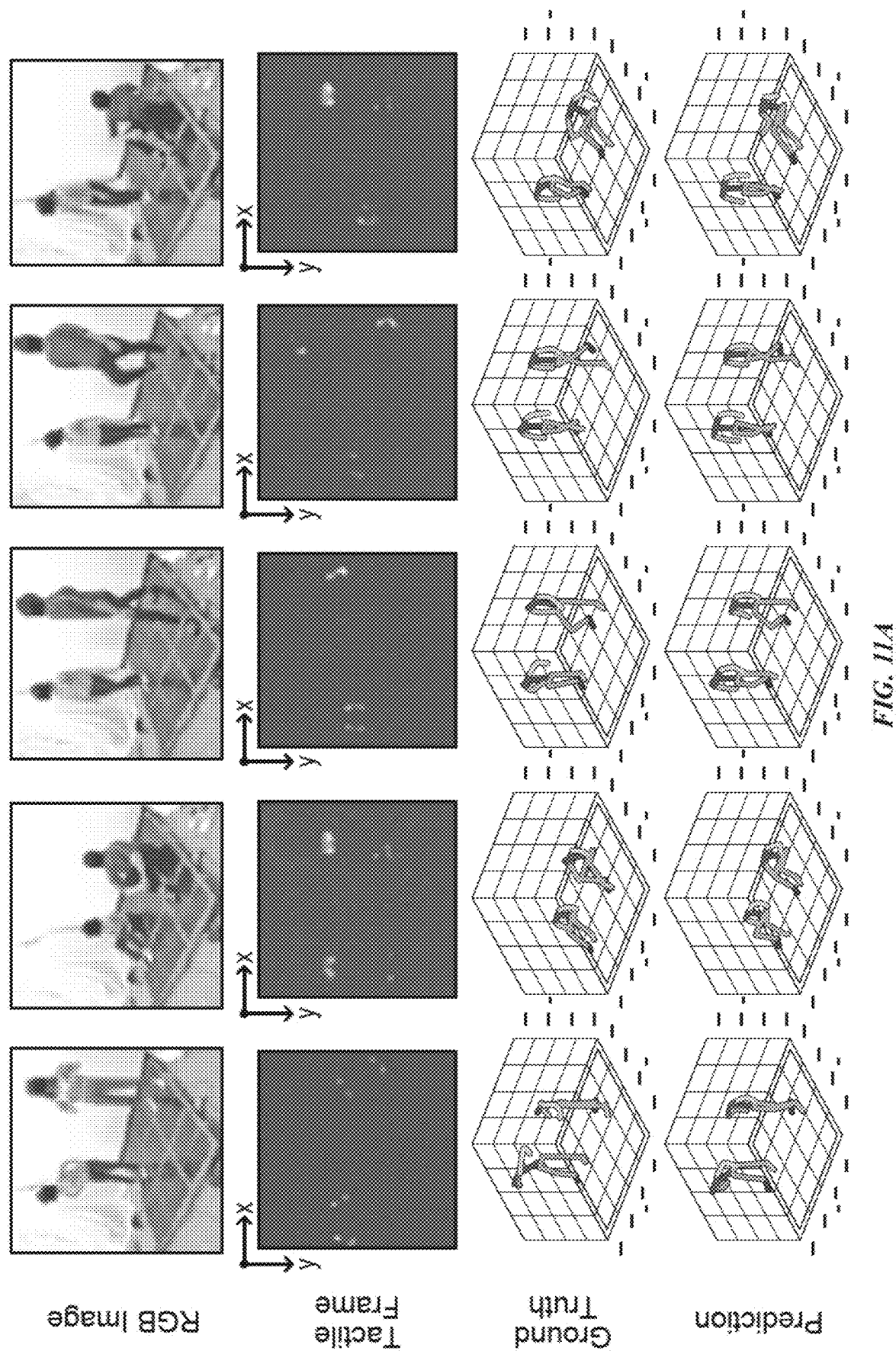
FIGS. 11A-11B show some qualitative results of exemplary multi-person 3D human pose estimation, where the images in FIG. 11B are a continuation of the sequence shown in FIG. 11A.
Figure 11B:
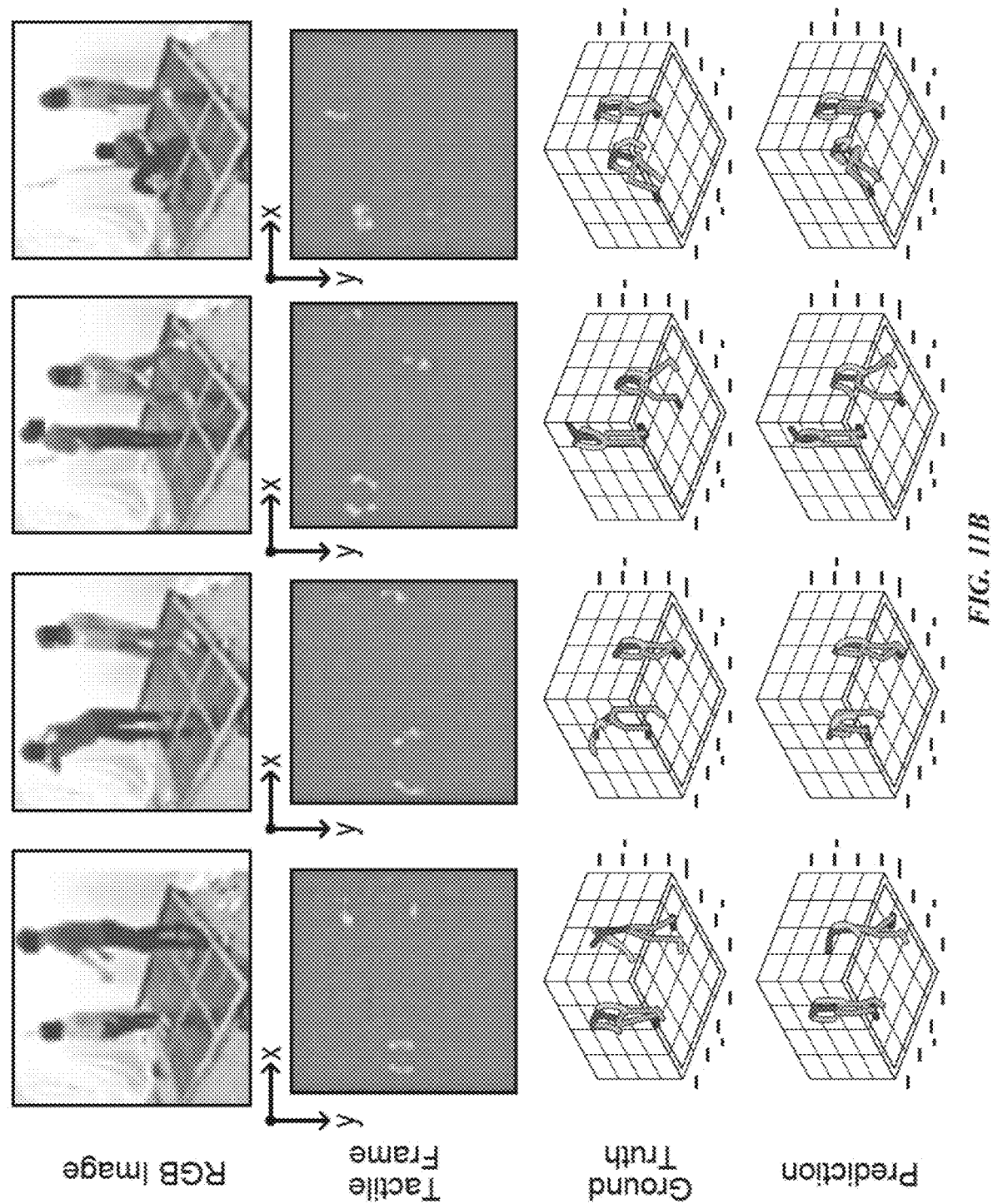

FIGS. 11A-11B show some qualitative results of exemplary multi-person 3D human pose estimation including, from top to bottom, the RGB image for ground truth annotation, the captured tactile frame, the ground truth 3D skeleton, and the predicted 3D skeleton from the model using only the tactile frames (unit: cm). The images in FIG. 11B are a continuation of the sequence shown in FIG. 11A. The network learns to localize each individual and predict the corresponding 3D pose. Purely from the tactile information, the network successfully localizes each individual and predicts his or her 3D pose with a localization error of less than about 15 cm. The predictions do not rely on any visual information and, therefore, are unaffected by visual obstructions or a limited field of view, which are common challenges in vision-based human pose estimation.

The prototype system was necessarily limited, for example, by the limited input datasets used to train the system in terms of both the limited number of subjects recorded and the limited number of activities recorded. As a result, the prototype system expectedly showed various "failure" cases, which actually help in demonstrating how the system works and how the system can be expanded with additional input training sequences. FIGS. 12A, 12B, 12C, 12D, and 12E show typical "failure" cases encountered in the prototype system. The typical failure cases can be categorized into three main types. First, the model fails to predict the position of the waist and the head (FIG. 12A). This is expected as it can be observed that the pressure distributions of the tactile maps are rarely or not affected by the movement of the head and wrist when a person is standing on feet. Also, the model fails to predict the poses where actions are performed without notable physical contact with the floor, e.g., free-floating legs during sit-ups and twisted torso during the standing-up process (FIGS. 12B and 12E). Furthermore, different actions may induce very similar pressure imprints, e.g., bending and twisting, causing trouble for the model to distinguish the activities due to the intrinsic ambiguity of the tactile signal (FIGS. 12C and 12D). As for the multi-person pose estimation, additional errors can happen because of the ambiguity underlying the tactile signals from different individuals, where the model fails when two people are too close to each other. Generally speaking, these failure cases are not inherent failures of the prototype system itself but instead can be attributed in large part to the limited content of the synthetic training dataset for the prototype system. It is anticipated that these "failures" could be circumvented by virtue of processing additional datasets in view of the present disclosures to arrive at further successful human pose predictions.

Furthermore, even with the constraint on the human body link lengths, some predicted human poses appear unrealistic in real life. The foregoing notwithstanding, it is anticipated that the present disclosures will further support improved predicated 3D pose estimation by imposing adversarial robustness as a prior to further constrain the predicted 3D human pose.

Also, while the prototype system used the same model for both single-person and multi-person pose estimation, this approach suffers from the ambiguity of the tactile signal induced by multiple people that are too close to each other. To obtain more accurate predictions on multi-person pose estimation, a region network can be applied to localize the tactile information belonging to each of the individuals, which will then respectively pass through the pose estimation network to predict the pose of each person. Further details about how this can be accomplished would be understood by a person skilled in the art in view of the present disclosures, including the materials incorporated herein by reference.

It should be noted that once the model is trained on an appropriate dataset, 3D pose estimation can be performed dynamically based on tactile information obtained from an intelligent carpet or other appropriate sensor system in real-time. Furthermore, 3D pose estimation systems and methods can be configured or trained to characterize poses and correlate them with specific actions. For example, the system might be trained to associate a particular pose with a particular action and could be configured to generate a signal upon detecting certain actions, e.g., hand and body motions might be used as inputs in a video game system, or a pose suggestive of someone wielding a handgun might be used by a security monitoring application (e.g., in a home, bank, store, government building, etc.) to generate an alert. Thus, for example, 3D pose estimation systems and method of the types described herein can be used in a wide range of potential applications including, without limitation, action recognition, smart homes, healthcare, and gaming, to name but a few.

Thus, 3D pose estimation systems and methods of the types described herein can employ a low-cost, high-density, large-scale tactile sensing carpet or other sensing system for sensing interactions between a subject and the ground and, leveraging perception results from a vision system as supervision, can learn to infer 3D poses using only the tactile readings of the subject interacting with the ground. Such systems and methods introduce a sensing modality that is different and complementary to vision-based systems, opening up new opportunities for pose estimation unaffected by visual obstructions and video-based privacy concerns in a seamless and confidential manner.

It should be noted that while various aspects are described with reference to the use of a tactile sensing floor covering, the same or similar concepts (e.g., recording pressure and/or other tactile information and training a neural information processing system based on synchronized video or other training data) can be used with sensor systems that can be placed on the subject in order to record the subject's interactions with the ground, such as, for example and without limitation, "wearable" devices incorporating sensor systems (e.g., socks, footwear, footwear insoles/inserts, bandages or other medical wraps/devices, etc., some examples of which are described in detail below) and sensors that can be attached to the subject or otherwise placed between the subject and the ground (e.g., a base or footings incorporating sensors such as for a machine or robot).

The present disclosure also provides for textiles made from functional fibers capable of acting as sensors. The sensors allow the textiles to be "smart textiles." While textiles such as garments having sensors exist, the textiles resulting from the present disclosures fit and act to a user just as a "non-smart" textile would while providing the benefits of a "smart textile." This is in contrast to existing "smart textiles," which are typically more rigid and/or not manufacturable in a scalable way. While existing "smart textiles" typically employ techniques such as weaving and embroidery to form their textiles, the present disclosure employs knitting as its technique for manufacturing its "smart textiles." Weaving interlocks its fibers in a manner such that the resulting textile is not stretchable or flexible in any meaningful manner. Garments having arbitrary shapes such as gloves and socks are not typically woven because it would be difficult to do and/or would result in a stiff, uncomfortable, and possibly not useable garment. A manufacturer would have to make sheets of woven materials and sew them together to create a garment like a glove or sock using weaving. Knitting, on the other hand, creates loops that interconnect, thus allowing for three-dimensional geometries to be more easily created. Garments having arbitrary shapes such as gloves and socks can be knitted. The result is garments that are flexible, wearable, and not stiff, contrary to yarn, which would be considered stiff in such contexts and likely could not be used with the techniques provided for in the present disclosure. Weaving needs additional tailoring of multiple pieces to form an actual garment, while knitting can directly fabricate the whole garment, providing for easier fabrication of garments. Additionally, weaving is generally limited to flat surfaces and monotonous surface textures, while knitting allows for the conformal design of complex 3D geometries and versatile surface textures. Still further, the knitting techniques provided are scalable in a manner that allows such smart textiles to be mass produced using automated machines to do the knitting, a feature not achievable using existing smart textile-making techniques, such as embroidery.

It should be noted that sensor systems used for 3D pose estimation as discussed above (e.g., carpets, mats, socks, shoe insoles/inserts, bandages, flooring, etc.) can include or be fabricated with fibers or textiles having sensors including functional fibers of the types described herein. It also should be noted that calibration techniques described herein can be applied equally to 3D pose estimation systems and methods such as for characterizing and calibrating a pressure-sensing carpet or mat.

As described herein, functional fibers that include a conductive core (e.g., a stainless steel thread) and a piezoresistive coating (e.g., a polydimethylsiloxane elastomer) disposed around a circumference of the core are well-suited for use with the knitting techniques provided for forming garments having arbitrary shapes. Further, the combination of the functional fibers and the knitting techniques means that the smart textiles can be fabricated in an automated manner, allowing for the mass production of smart textiles that function akin to counterpart textiles that do not include sensors or are not otherwise "smart." As used herein, "automated" includes being able to fabricate or otherwise produce an object, function, etc. without any human labor intervention. The fabricated garments can be referred to as whole-garment sensing because the entire garment can be fabricated from the functional fibers, meaning the whole garment can provide sensing capabilities. Alternatively, the functional fibers can be incorporated into garments at select locations as desired to create garments having certain areas or zones where sensing is desirable. The systems and methods provided for herein allow for creation of garments and other textiles that provide a sensing platform across virtually an entire surface area of the garment/textile, the sensing platform being high-density, 3D-conformal, and low cost.

Fiber Fabrication+Knitting

Figure 13:
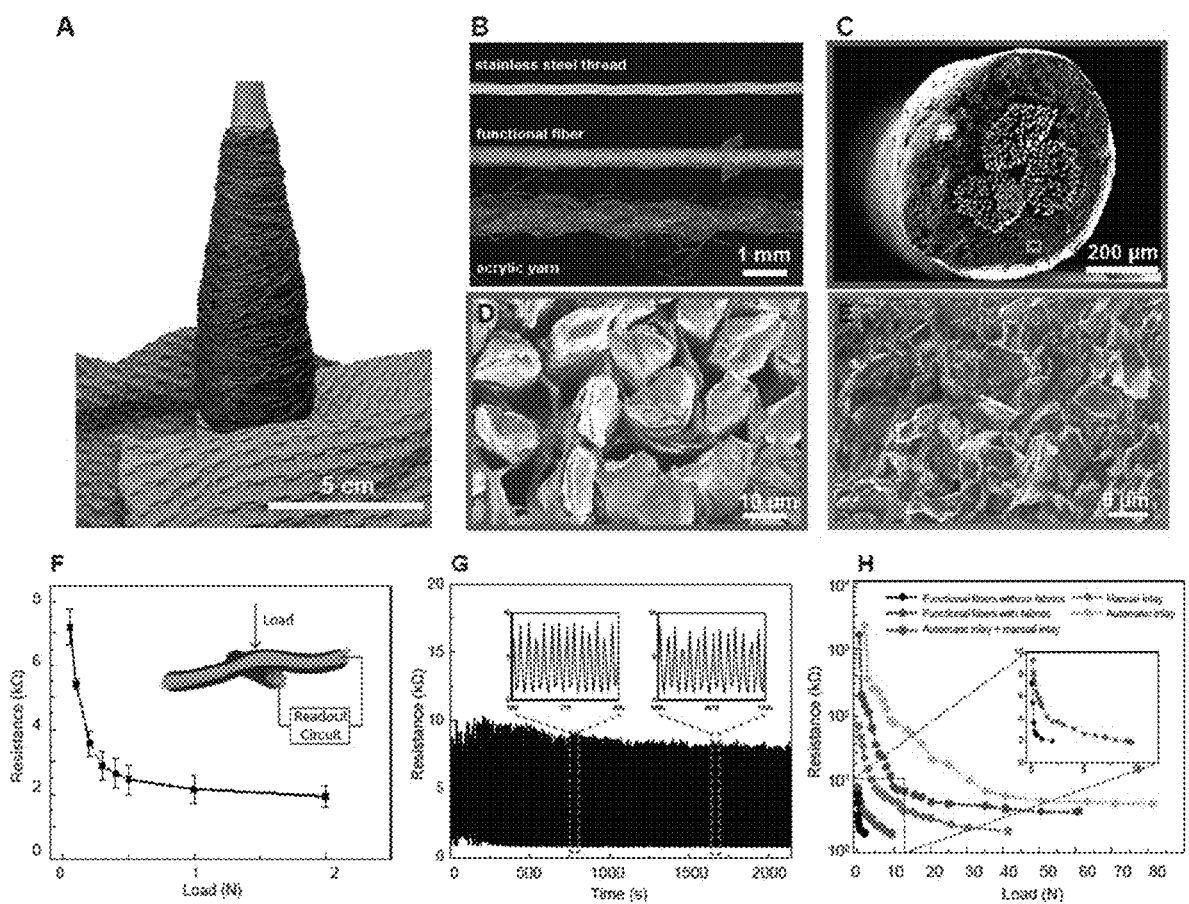
FIG. 13 shows exemplary embodiments of coaxial piezoresistive fibers, where

FIG. 13A illustrates a coaxial piezoresistive fiber produced using a continuous fabrication method for low-cost (about 0.2 US dollar/m). The continuous fabrication method can be an automated fiber-pulling set-up. FIGS. 13B and 13C provide for one non-limiting example in which a commercial conductive stainless steel thread, shown in FIG. 13B, is coated with a piezoresistive nanocomposite, shown in FIGS. 13C, 13D, and 13E. More specifically, FIG. 13B illustrates a morphology of each of: (a) a stainless steel thread; (b) a functional fiber, such as the stainless steel thread being coated by a piezoresistive nanocomposite; and (c) an acrylic yarn. The piezoresistive nanocomposite can include, for example, a polydimethylsiloxane (PDMS) elastomer as the matrix and graphite/copper nanoparticles as the conductive fillers. The cross-section of the functional fiber shown in FIG. 13C illustrates the stainless steel thread as a central portion of the fiber with the PDMS elastomer encompassing a circumference of the thread. Magnified views of the functional fiber are shown in FIGS. 13D and 13E, with FIG. 13E in particular showing a uniform dispersion of nanoparticles that can be achieved, for example, after shear mixing the nanocomposite at a high rate of speed.

While the illustrated embodiment provides for a stainless steel core, the core can be any thread, filament, wire, or other configuration having conductive properties. Other metals and/or conductive polymers can be used in lieu of, or in combination with, stainless steel. Likewise, while the illustrated embodiment provides for a piezoresistive coating that includes PDMS, the coating can be any thermoset or thermoplastic that achieves similar effectiveness. For example, the coating can be a polymer that is impregnated or otherwise filled with fillers to give it changing resistive properties with respect to some external signal. Further, while in the present disclosure pressure changes are sensed and relied upon to make various determinations and predictions, alternatively, or additionally, other properties can be used too. For example, changes in temperature, a pH level, a chemical level, an electro-magnetic property, an acoustic parameter, a vibration, etc. are other parameters that can be sensed, and thus the formulation of the fiber coating can be adapted in conjunction with the same. Still further, multiple fibers that sense different signal types can be included in the same garment and/or materials, such as a carpet and the like, described above, conducive to detecting changes in multiple properties can be utilized for the coating.

Each sensing unit can be constructed by orthogonally overlapping two piezoresistive fibers. FIG. 13F illustrates the electrical characteristic of a single sensor composed of two such coaxial piezoresistive fibers. As shown, such a configuration can convert pressure (normal force) stimuli into electrical signals exhibiting a resistance drop (approximately in a range from about 8 kΩ to about 2 kΩ) when a force approximately in the range of about 0.05 N to about 2 N is applied. FIG. 13G demonstrates that no decrease in performance is observed in the functional fiber even after more than 600 load and unload cycles. The sensor characteristic is stable and reliable over at least that usage/time frame. FIG. 13H illustrates an electrical characterization on devices composed of different combinations of fabric structures, including manual inlays, automatic inlays, a combination of automatic and manual inlays, functional fabrics with fabrics, and functional fibers without fabrics. The performance (e.g., sensitivity and detection range) of the functional fiber is affected, at least in part, by the processing parameters (e.g., pulling speed, pressure, and coating thickness, as shown in Fig. S1 of Appendix B of the provisional patent application from which the present application claims priority) and materials compositions (e.g., copper and graphite weight percentage, as shown in Fig. S1 of Appendix B). The functional fiber can be stable at room temperature (up to about 50° C.), but its resistance can increase with temperature afterward, as also shown in Fig. S1 of Appendix B.

The formed functional fibers can then be seamlessly integrated into fabrics and full garments through programmable digital machine knitting. Due to the interlocking loops (or stitches), knitted fabric enjoys additional softness and stretchability as compared with woven fabric. A plurality of functional fibers knitted together as provided for herein can be referred to as a "knit." Furthermore, machine knitting can realize versatile surface textures, complex 2D/3D shapes and geometries, as well as maximal conformability during wearing, enabling the scalable fabrication of full-garment wearables that are compatible with daily human activities. The functional fibers can also be integrated into smart carpets and the like, as described in greater detail above.

Figure 14:
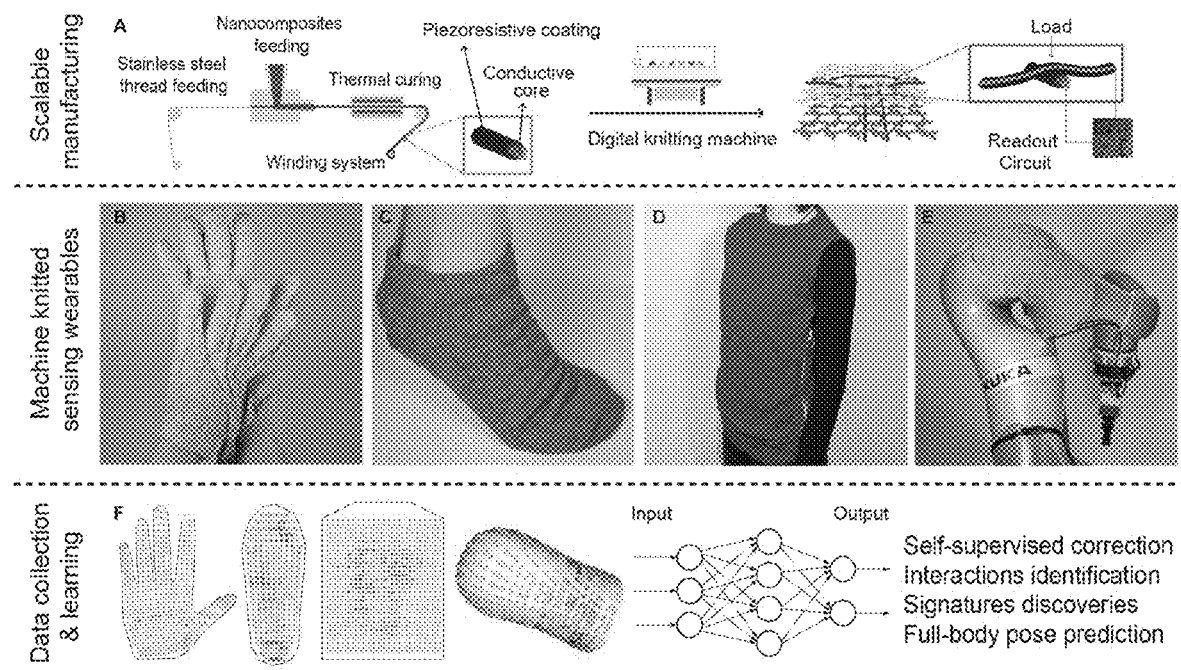
FIG. 14 shows scalable manufacturing of machine knitted sensing wearables such as for data collection and learning, where

To accommodate the mechanical characteristics of the piezoresistive functional fiber, a knitting technique, inlaying, can be employed. Performed automatically on a knitting machine, inlaying horizontally integrates the yarn in a substantially straight configuration, which cannot be directly knitted by forming loops due to their relative fragility and stiffness. In some embodiments, to optimize the manufacturability and device performance, two methods of inlaying can be employed: automatic inlaying and manual inlaying. Additional information related to the same can be found in Appendix B, such as the portion associated with Fig. S4. Two knitted fabrics with functional fiber inlaid in orthogonal directions can be assembled as a sensing matrix. Referring again to FIG. 13H, and as also shown in FIG. 14, sensor sensitivity and detection range can be highly influenced by the knitted pattern. Generally, sensitivity decreases and detection range increases with the integration of fabrics. A sensor composed of two fabrics with automatic inlaid functional fibers can have the lowest sensitivity and highest detection range, for instance, because the ribbed texture can create a gap between two fabrics and lower the force response.

FIG. 14A illustrates one non-limiting example of a scalable manufacturing technique that can be used to form wearable garments that utilize functional fibers like those described above. A person skilled in the art, in view of the present disclosures, will recognize such techniques can also be applied to manufacturing a carpet and other objects provided for herein or otherwise derivable from the present disclosures. As shown, a stainless steel thread can be fed forward using a fiber-feeding, or fiber-pulling, system, such as by a pulley in conjunction with a winding system, to a location where the coating is applied. The fiber-pulling system can be customized as desired such that it can an provide length-scale coaxial piezoresistive fiber fabrication and digital knitting processes for seamless integration of sensing matrices in fabrics and garments. The coating in the illustrated embodiment is nanocomposites fed onto the thread. Many techniques known to those skilled in the art for applying a coating to a fiber or thread can be employed. The combination of the thread and the nanocomposites can then be cured. In the illustrated embodiment, the curing occurs further down the manufacturing line and is done thermally, although in other embodiments the curing can occur at the location where the coating is applied to the thread and/or other techniques for curing can be employed. A person skilled in the art will appreciate other techniques and configurations can be used to advance or otherwise move the stainless streel thread to a location where a coating will be applied. A fiber-feeding system can be any combination of components (e.g., gears, pulleys, belts, etc.) operable to advance the stainless steel thread (or other component being used to form a conductive core of a functional fiber) in conjunction with forming the functional fiber and/or manufacturing a textile with a functional fiber (referred to herein as a transport system). The result of the cured coating on the stainless steel thread is a functional fiber that includes a conductive core and a piezoresistive coating. FIG. 14A further shows a digital knitting machine that can be used to combine a plurality of functional fibers together to form a wearable, such as a garment, having sensors disposed throughout the wearable. Thus, the illustrated embodiment of FIG. 14A provides one non-limiting example of an inexpensive large-scale manufacturing system and method to create tactile sensing textiles.

Many wearables (e.g., garments) can be formed in view of the present disclosures. Some non-limiting examples are provided in FIGS. 14B-14E. As shown, large-scale tactile sensing matrices can be embedded into full-sized gloves (e.g., 722 sensors, FIG. 14B), socks (e.g., 672 sensors, FIG. 14C), vests (e.g., 1024 sensors, FIG. 14D), and robot arm sleeves (e.g., 630 sensors, FIG. 14E). A commercial digital knitting system, which is known to those skilled in the art, can allow these types of garments to be fully customizable, thus allowing for garments tailored based on an individual size and/or an individual preference(s) (e.g., color, particular design features), meeting the needs of personalization and fashion design. Details about the knitting operation and designs can be found in Appendix B, such as the portion associated with Figs. S3-S5. In at least some embodiments, a modified electrical-grounding-based circuit can be used to extract signals from each individual sensor.

To the extent the present disclosure describes garments as being wearable, a person skilled in the art will appreciate that other garments or textiles that are not necessarily wearable by a human can also be produced in accordance with the present disclosures. By way of non-limiting examples, the garments produced based on the disclosed systems and methods can be placed on objects like robots (or portions thereof), machines, furniture, vehicle seats, and/or on floors and/or walls to sense some sort of action. By way of further non-limiting examples, the garments produced based on the disclosed systems and methods can be used in garments for animals, such as clothing, saddles, etc. Accordingly, the term "wearable garment" can encompass any garment or textile that can be placed on and/or over an object, human, or animal that allows some sort of action to be sensed.

FIG. 14F illustrates that the provided for systems and methods allow for the collection of large tactile datasets (up to a million frames or even more) over versatile human-environment interactions. More particularly, FIG. 14F illustrates the data flow of the data pipeline to understand human activity and pose classification, showing input data from different garments going into a neural network, with the output including classifications identified above. Such disclosures can also be applied to carpets and the like, as provided for above. Each sensor can be represented by a circle, and as pressure is applied, an indication of where the pressure is being applied can appear, such as by using various colors and/or intensities of colors to reflect changes in resistance. As provided for herein, the present systems and methods, and the wearables and other object (e.g., carpets) that are produced using the same, can be coupled with machine learning techniques, self-supervised sensing correction, physical interactions identification, human behavior signatures discovery, and/or full-body motion predictions to provide even further benefits from and/or for the wearables. Examples of some of these benefits are described in greater detail below and/or the Appendices. For instance, detailed network architectures are illustrated in FIG. S7 of Appendix B.

Self-Supervised Sensing Correction/Calibration

Figure 15:
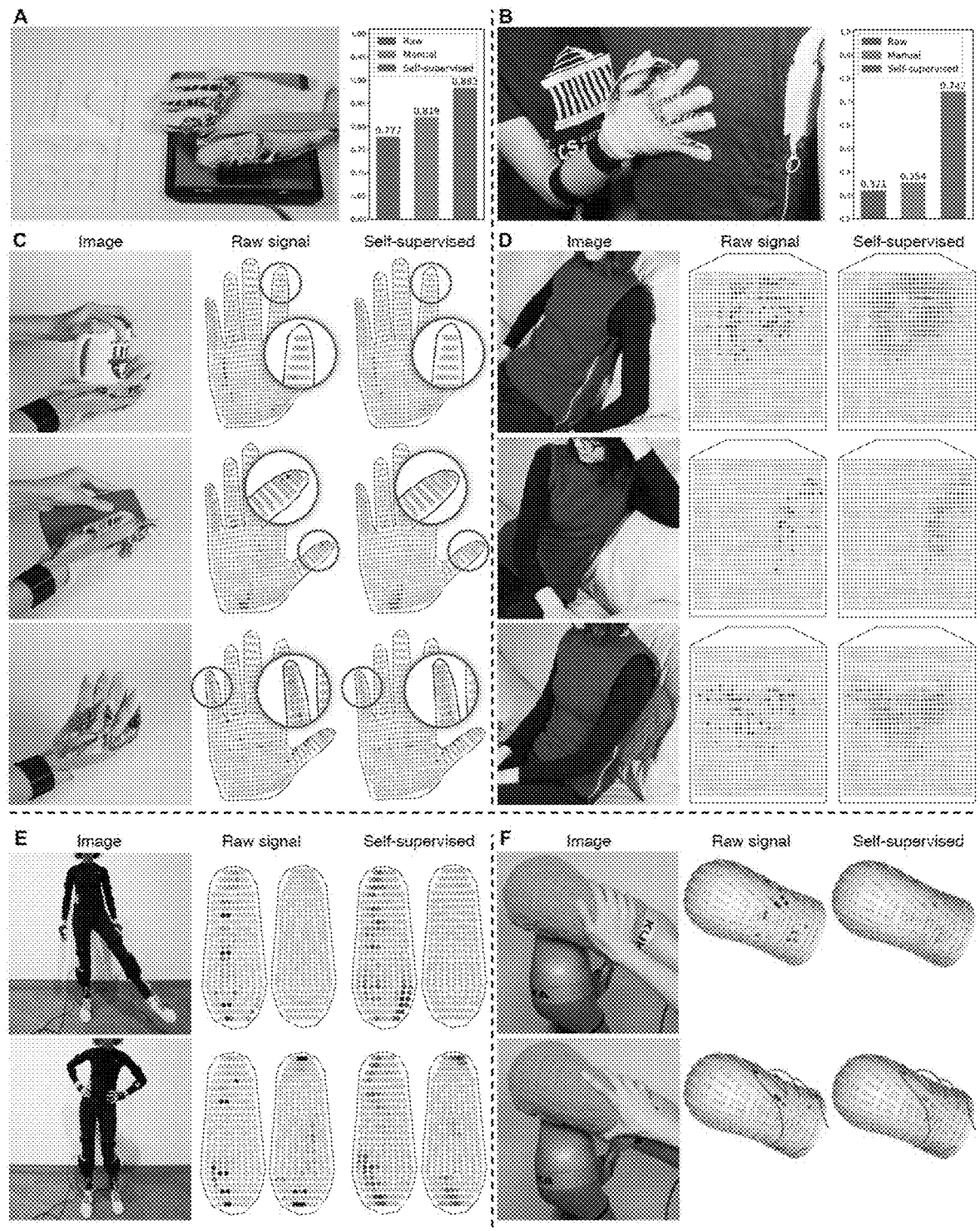
FIG. 15 shows various forms of collecting tactile information using sensing wearables, where

While researchers have attempted to fabricate flawless sensor arrays, sensor variation and failure have been inevitable during scale-up and daily applications. In contrast, living organisms can adapt their sensory system in the presence of individual sensor failure or variation. The present disclosure provides for a similar mechanism that can relax current strict standards in sensor fabrication. Restricted by high-density sensing units, complex geometries, and diverse application scenarios, it is impractical to perform individual correction of each sensor in the provided embodiments. Thus, a self-supervised learning paradigm is provided that learns from weak supervision, using spatial-temporal contextual information to accommodate malfunctioning sensors and compensate for variation. More particularly, synchronized tactile responses are collected from the garment(s) (e.g., the glove) and readings from a digital scale pressed by a wearer, as shown in FIG. 15A and, as referenced in Appendix B, data S2. At each frame, the scale reading indicates the force being applied, which is expected to linearly correlate with the sum of tactile responses at all sensing points. A fully convolutional neural network (FCN) can be trained to take in a small sequence of raw tactile array responses and output a single frame with the same spatial array resolution, representing the calibrated result of the middle frame of the input sequence (as shown in FIG. S7A of Appendix B). The neural network can be optimized via a stochastic gradient descent (SGD) with the objective having two components: one can encourage the output to preserve the details in the input and the other can restrict the calibrated tactile response to be close to the reading from the scale. The network can increase the correlation between the tactile response and the reference (reading from scale). In one exemplary embodiment, illustrated by FIG. 15A, as well as FIG. S8, A to D, of Appendix B, the correlation was increased from approximately 77.7% to approximately 88.3% for the glove, and from approximately 92.4% to approximately 95.8% and from approximately 75.9% to approximately 91.1% for the left and right socks, respectively.

The same self-supervised learning framework can be employed using the corrected glove as a new "scale" to process the sensing fabrics with arbitrary shapes, such as a vest and robot arm sleeve, as shown in FIG. 15B and, as referenced in Appendix B, data S2). In this illustrated exemplary embodiment, the correlation was increased from approximately 32.1% to approximately 74.2% for the vest and from approximately 58.3% to approximately 90.6% for the robot arm sleeve (see also FIG. S8E of Appendix B).

The self-supervised calibration network can exploit the inductive bias underlying the convolutional layers, can learn to remove artifacts, and can produce more uniform and continuous responses, as supported by FIGS. 15C-15F, as well as FIG. S9 of Appendix B. Further, the provided for calibration network enables the large-scale sensing matrix to be resistant to individual variation and even disruption, and therefore ensures the quality of extracted information.

Figure 17A:
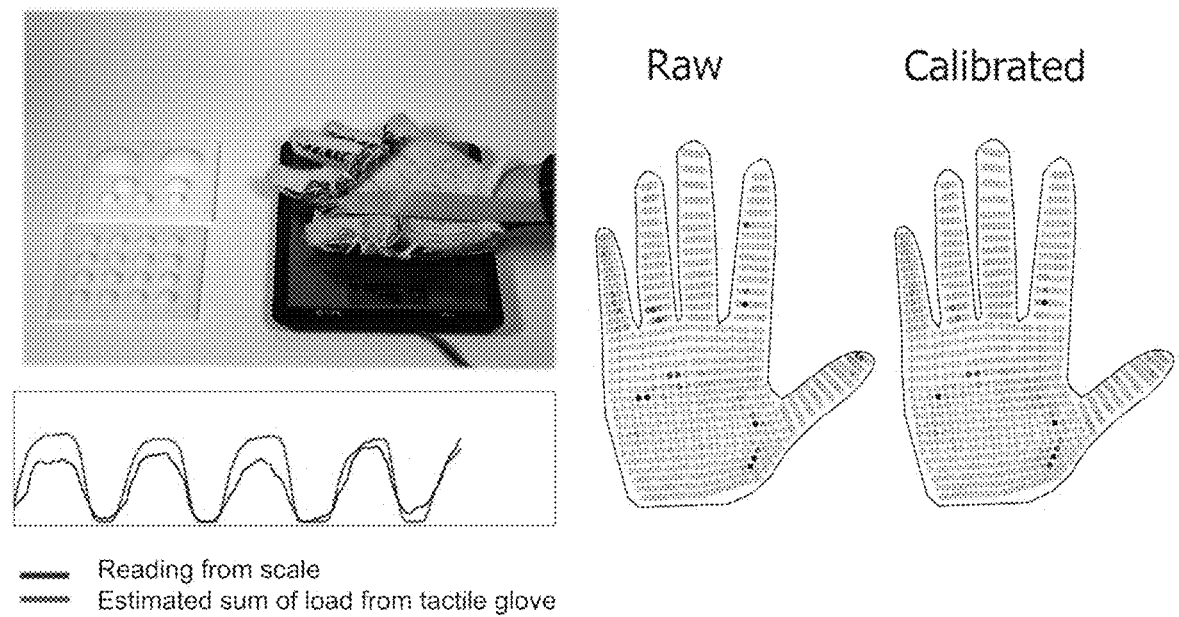
FIG. 17A illustrates one exemplary embodiment of calibrating a sensing wearable glove using a digital scale.

FIG. 17A illustrates an additional example of calibrating a glove. It is a snapshot from a video that illustrates the estimation of the load calculated form the glove readout compared to the scale readout. As shown, the glove is again used in conjunction with a digital scale, with the wearer of the glove applying a force to the scale at various angles, positions, etc. The data can be collected and calibrated in accordance with the present disclosures.

As shown by FIG. 15B, the calibrated glove can become a new "scale" for calibrating other garments, such as a vest and/or robot arm sleeve. Similarly, one or more other datasets can be collected by pressing the target garment using the calibrated glove, whose responses can be regarded as the "reference," and train another calibration network using the same network architecture and training procedure. The tactile information from the calibrated glove can be collected and can reflect the physical force being applied while pressing on the tactile vest wearing the calibrated tactile glove. In some examples, like the one in FIG. 15B, correlation between the tactile response and the "reference" increases from approximately in the range of about 32.1% to about 74.2% for the vest after self-supervised calibration. Again, similar methods can be used with other wearables, such as the calibration of a sensing sleeve. In some instances, the correlation between the tactile response and the "reference" for the sleeve increase from approximately in the range of about 58.3% to about 90.6% for the robot sleeve. Examples of calibrated tactile response from a glove, a vest, socks, and a robot arm sleeve are provided in FIGS. 15C, 15D, 15E, and 15F, respectively. In each instance, artifacts are removed and matrix uniformity improves. As discussed above with respect to FIG. 14F, each sensor of the wearable can be represented by a circle in the raw signal and self-supervised images, with the sensors responding in some fashion when pressure is applied to them. In the illustrated embodiments, locations of pressure, and more specifically changes in resistance indicative of locations of pressure, are illustrated by different colors and/or intensities of colors, although other illustrations and/or indications are possible without departing from the spirit of the present disclosure. The self-supervised images result from the calibrations provided for herein.

The self-supervised calibration network can exploit the inductive bias underlying the convolutional layers, learn to remove artifacts, and produce more uniform and continuous responses, among other capabilities. It enables the large-scale sensing matrix to be resistant to individual variation and even disruption and therefore can ensure the quality of extracted information. As provided for herein, calibration can be used to fill-in holes where data is lost or otherwise corrupted.

While the illustrated embodiment provides for a glove, any type of covering for a hand can be adapted in a similar manner, including but not limited to mittens, wraps, or medical bandages. A person skilled in the are will also understand how to apply these same principles to carpets and the like in view of the present disclosures.

Classification+Signatures

The reliability, stability, and wearability of full-body sensing garments coupled with self-supervised calibration pipeline as provided for herein allows a large tactile dataset (over 1,000,000 frames recorded at 14 Hz) on versatile human-environment interactions to be collected. Such datasets can include data related to object grasping, complex body movement, and daily locomotion. The capability of the provided for systems and methods can be tested and demonstrated, by way of non-limiting examples, by extracting useful information for action identification, motion prediction, signatures discoveries, and environment classification.

Vest

A full-sized sensing vest (with 1024 sensors in one non-limiting embodiment) illustrated in at least FIGS. 15D and 16A shows the exact force distribution during sitting, standing, lying, and other actions, which can mirror a wearer's posture, activity status, and the shape/texture of the contacting object. With the increasing burden of healthcare, especially for the elderly and disabled, such smart wearables offer a solution as automatic health monitoring system, which can trigger an alarm in an emergency (e.g., sudden fall), warning, and/or provide information for early disease detection (e.g., heart attacks or Parkinson's disease). Notably, such alarms, warnings, detections can be implemented in any wearable produced in accordance with the present disclosures, and thus are by no means limited to vests. Also, because such wearable is soft and comfortable, it can be a suitable choice for infant movement/body position tracking and identifying potential neurodevelopmental disorders.

Figure 16:
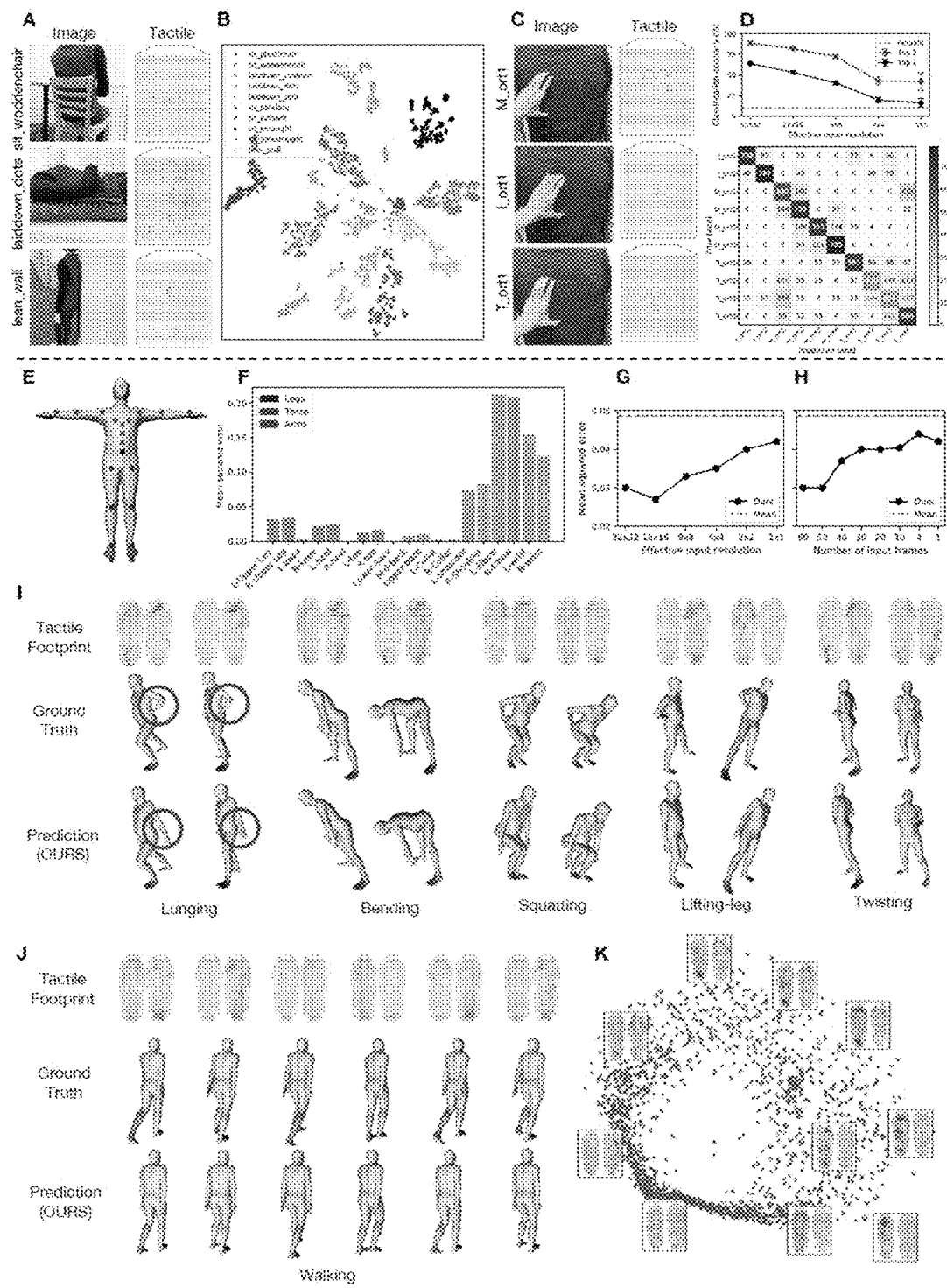
FIG. 16 shows some exemplary interpretations of tactile information, where

Furthermore, the sensing matrix provided for herein demonstrates a superior sensitivity than a human's back. By way of example, and as shown in FIG. 16B, a dataset can be collected by pressing models of three letters (e.g., M, I, and T) against the back of a mannequin wearing a tactile vest of the present disclosure from different orientations. The data can be categorized into 10 classes and a simple neural network that takes a small window of responses as input can be trained to determine and/or predict the type of the letter and the orientations. During some testing, the classification network demonstrated it can achieve an accuracy of 63.76%, which can drop as the effective resolution decreases from about 32×32 to about 1×1, as illustrated in FIG. 16. This illustrates the benefit of higher resolution as compared to a human's back.

Figure 17B:
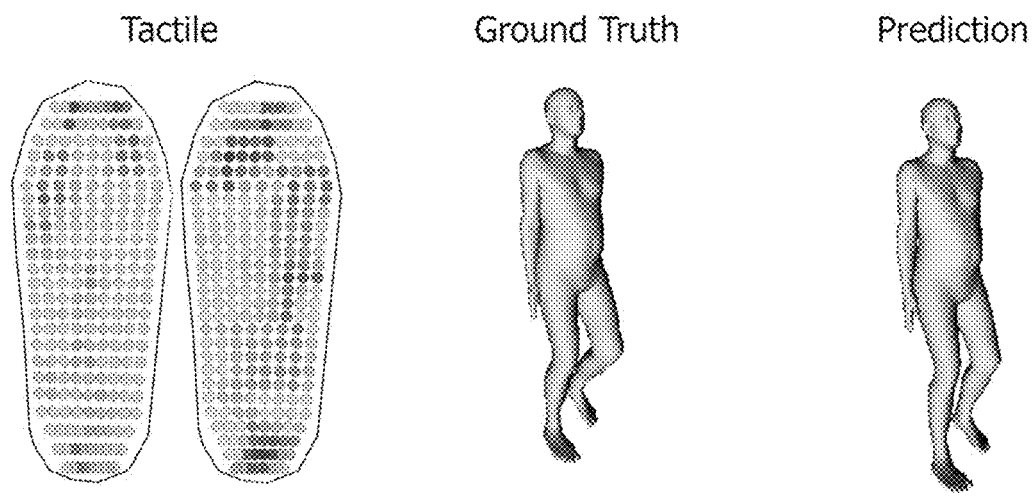
FIG. 17B illustrates one exemplary embodiment of using tactile feedback from sensing wearable socks to predict a stance of a wearer of the socks based on the tactile feedback.
Figure 17C:
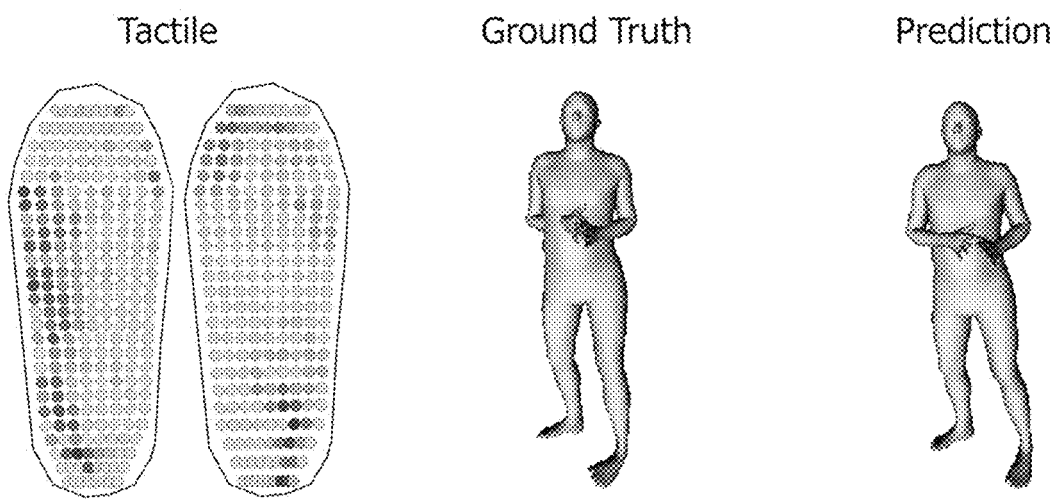
FIG. 17C illustrates another exemplary embodiment of using tactile feedback from sensing wearable socks to predict a stance of a wearer of the socks based on the tactile feedback.
Figure 17D:
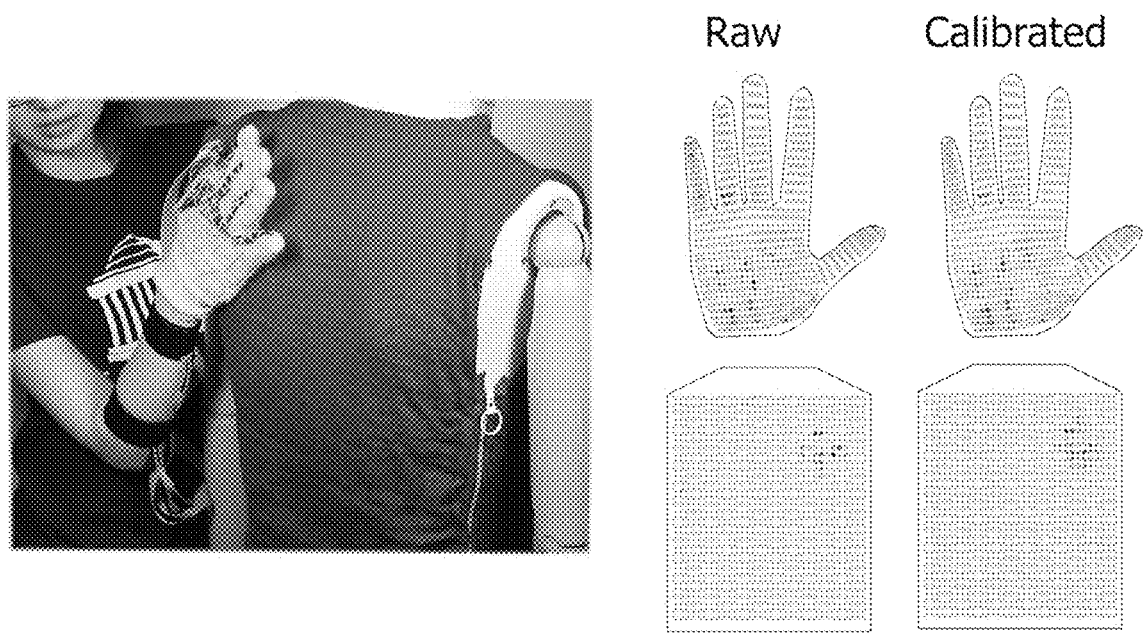
FIG. 17D illustrates one exemplary embodiment of calibrating a sensing vest using a calibrated sensing wearable glove.

FIG. 17D illustrates an additional example of calibrating a vest using a calibrated glove. As pressure is applied by the glove to the vest, sensors on each of the glove and the vest respond by changing colors and/or intensifying colors based on the amount of pressure experienced. The raw and calibrated data can be provided for both the glove and vest. More particularly, the concept of self-calibration, described above, allows the sensing garment to be calibrated with arbitrary geometry.

While the illustrated embodiment provides for a vest, any type of top can be adapted in a similar manner, including but not limited to shirts, coats, sweaters, sweatshirts, blouses, wraps, undergarments (e.g., undershirts, some types of t-shirts, bras, lingerie), or medical bandages. Likewise, these disclosures can also be applied to bottoms, including but not limited to pants, trousers, shorts, undergarments (e.g., underpants, long johns, lingerie), or medical bandages. Whole-garment sensing wearables can be extended into various industries and fields, and the garments associated with the same, to provide useful information for those fields, including but not limited to athletics (e.g., particular types of garments associated with different sports), construction (e.g., gear used on construction sites), medical (e.g., medical masks), and military (e.g., uniforms worn in training or combat). A person skilled in the art will appreciate that these disclosures can likewise be applied to objects outside of wearables, such as carpets and the like, as provided for herein and/or as derivable from the present disclosures.

Action Classification+Clustering

For example, human action identification can be achieved based on tactile information obtained from a pair of socks integrated with functional fibers. The dataset can be collected by the user wearing the sock and performing various daily activities, including walking forward, walking backward, side-walking, walking upstairs/hill, walking downstairs/hill, leaning, jumping, standing, standing on tiptoes, lifting a leg (as shown in top image of FIG. 15E), squatting, twisting, turning (as shown in bottom image of FIG. 15E), and bending over (e.g., to touch toes), among other actions that can be performed by a wearer of the sock(s). The system can take in a desired number of tactile frames retrieved from the left and right sock (e.g., 45 frames), each of which can be passed individually through two convolutional layers each followed by a rectified linear unit (ReLU) activation and maxpooling. The resulting hidden layers can be passed through a linear layer followed by a softmax to predict associated class of the task type. As discussed above, human action identification can also be achieved by way of a carpet or the like, in addition to or in lieu of socks or other footwear.

Motion Prediction

As discussed above, motion prediction can be achieved by the present systems and methods. Further illustrations related to the same are provided with respect to FIGS. 16, 17B, and 17C, as well as Fig. S14 and the referenced S5 movie from Appendix B. The systems (sometimes referred to as a network) provided for in the present disclosure are able to differentiate patterns of footprints across different actions, and thus the capability of tactile socks, carpets, floors, etc. can be further tested by training a similar system (or network) to predict a human's pose.

Humans maintain the dynamic balance of the body by redirecting the center of mass and exerting forces on the ground, which results in distinct force distributions on the feet. A person's pose can be estimated from a change of force distribution over time obtained by tactile socks as provided for herein as a sequence of pressure maps. For example, the body pose can be represented by 19 joint angles spanning over the legs, torso, and arms. Synchronized tactile data from a pair of sensing socks and a full-body motion capture (MOCAP) suit can be recorded, while the user performs versatile actions. The pose prediction task can be modeled as a regression problem using a convolutional neural network. The model can process a time-series of tactile array footprints that can contain the evolving information about the contact events and can predict the human pose in the middle frame. The neural network can be optimized by minimizing the mean-squared error (MSE) between the predicted and the ground truth joint angles (MOCAP data) using SGD. Further details can be found in Appendix B and the descriptions and references to figures below.

FIG. 16A illustrates example photographs and tactile frames that can assist in the identification of diverse sets of signatures, such as discussed above. FIG. 16B provides a T-SNE plot from the pose dataset from the tactile vest, described above. The separable clusters illustrate the discriminative capability of the sensing vest.

FIG. 16C provides example photographs and tactile frames of the letters "M," "I," and "T" pressed on the tactile vest for classifying the letter and the orientation. FIG. 16D provides a confusion matrix, illustrating that accuracy drops as effective resolution decreases.

FIG. 16E is an illustration of 19 different joint angles that can be predicted by a model as provided for herein. FIG. 16F provides for the MSE in pose production. As shown in FIGS. 16G and 16H, there can be an influence of sensor resolution and number of input frames (context window), respectively, on prediction performance. The dashed line in each figure represents a baseline performance where the predictions are the canonical mean poser obtained from the training data.

FIG. 16I provides a comparison of various poses reconducted from MOCAP (ground truth) and tactile frames from the socks as provided for herein (prediction). Discrepancies in predicting the pose of the arm are circled.

FIG. 16J provides for a time series prediction of walking in view of the present disclosures, and FIG. 16K provides principal component analysis (PCA) on tactile maps from walking, with the insets corresponding to tactile frames.

FIGS. 17B and 17C illustrate two examples of motion prediction of a user wearing tactile socks is made based on tactile feedback from the sensors in the socks. In FIG. 17B, the tactile feedback of the sensors is illustrated, an image of the stance of the person providing the force on the tactile socks is shown (the "Ground Truth"), and an image of what the model predicts the stance of the person providing the force on the tactile socks is provided. The prediction and actual stances are strikingly similar. FIG. 17C is presented in a similar manner, with the tactile feedback of the sensors illustrated, an image of the stance of the person providing the force on the tactile socks shown as the "Ground Truth," and an image of what the model predicts the stance of the person providing the force on the tactile socks is provided. Again, the prediction and actual stances are strikingly similar, even down to the placement of the hands.

While the illustrated embodiment provides for socks (also referred to as stockings), any type of foot covering can be adapted in a similar manner, including but not limited to shoes, boots, slippers, or medical bandages. Likewise, and as described in greater detail above, the present disclosures allow for these determinations to be made by way of a carpet, floor, or other similar objects.

Robot Arm

In addition to the sensing wearables described herein, the systems and methods disclosed can also work as skin for a robot. Most modern robots rely solely on vision; however, in the fields of robot manipulation and human-robot interaction, large-scale and real-time tactile feedback can be a critical component for more dexterous interaction skills, especially when vision is occluded or disabled. The sensing wearable can enable conformal coverage on the robotic gripper, limbs, and other functional parts with complex 3D geometries, endowing the robots with a strong tactile sensing capability. FIG. 15F illustrates a robot arm (sometimes referred to herein or elsewhere as "KUKA") equipped with the conformal sensing skin of the present disclosure. The robot arm can receive real-time tactile feedback and can feel the touch of a human being. It obtains huge potential in unobtrusive multi-point collision and interaction detection, as shown in FIG. 18, which remains challenging with the embedded torque sensors in the robot arm and conventional computational tools. Therefore, the present systems and methods step up as an important ingredient to facilitate future cooperation between humans and robots (or service robots).

The sleeve can serve as a skin of the itself, or alternatively, the outer-most layer of a robot can be configured to have a textile like the sleeve as part of it to form the skin of the robot. This can allow for desired tactile feedback for the robot, and the host of applications that can result from the same.

Figure 17E:
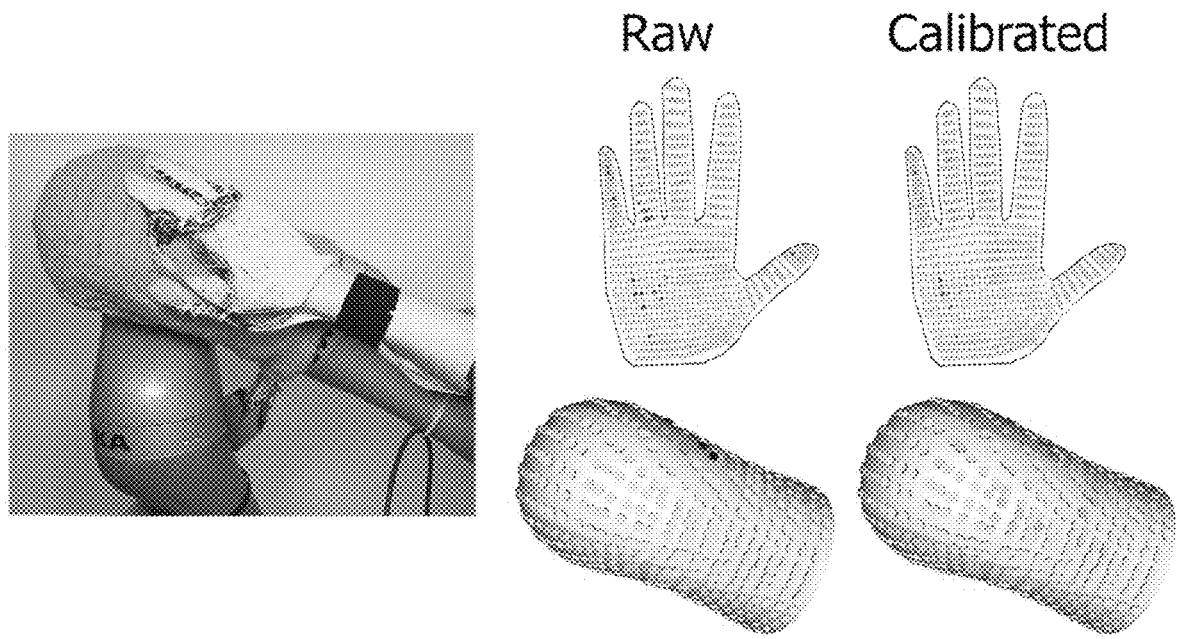
FIG. 17E illustrates one exemplary embodiment of calibrating a sensing sleeve using a calibrated sensing wearable glove.

FIG. 17E illustrates an additional example of calibrating a sleeve using a calibrated glove. As pressure is applied by the glove to the sleeve, sensors on each of the glove and the sleeve respond by changing colors and/or intensifying colors based on the amount of pressure experienced. The raw and calibrated data can be provided for both the glove and sleeve.

The results attributable to the present disclosures demonstrate a broad utility of the integrated platform coupling scalable manufacturing and computational pipeline and highlight its potential in human-environment interaction learning, which is an integral step toward the convergence of human and artificial intelligence. Certain exemplary embodiments bridge the gap between functional fibers and industrial-scale textile manufacturing, enabling monitoring, recording, and understanding of human daily behaviors and activities. The present disclosures allow for training data to be recorded and analyzed in a wide variety of contexts. For example, training data of baseball players with wearable tactile gloves can be recorded and analyzed for optimized training strategy. Once combined, the platform provided for by the systems and methods herein allows full-body data collection, including systematic information on human movement, and diverse human-environment interactions, which may lead to breakthroughs in healthcare, robotics, service robots, human-computer interactions, biomechanics, education, and smart interactive homes, among other industries and uses.

While various exemplary embodiments focus on garments, any type of textile can be fabricated, calibrated, and used in accordance with the present disclosures. Some non-limiting examples of such textiles include carpet and furniture. The type of garments that can be used in conjunction with the present disclosures is essentially limitless. As discussed above tops, bottoms, gloves, and socks can all be formed using the systems and methods provided for herein, as can other types of garments not explicitly described or illustrated, such as headwear (e.g., hats, caps, wraps, medical bandages), among other garments worn by humans, animals more generally, robots, or machines more generally.

Further, the present disclosure provides for sensors that enable identifying and/or predicting human activity, but they are by no means limited to use with human activity. The systems and methods provided for herein can also be used in the context of a control system, such as by providing sensor feedback to allow for parameters to be monitored and/or actions to be taken in response to the same. By way of further non-limiting example, the systems and methods provided for herein can be used to identify activities and/or events having to do with animals, robots, machinery, and/or in an environment.

The priority patent application, along with any descriptions and claims provided for herein, provide the relevant description of the various disclosures of the present patent application. One skilled in the art will appreciate further features and advantages of the invention based on the above-described embodiments and the content of the priority patent application. Accordingly, the invention is not to be limited by what has been particularly shown and described, except as indicated by the appended claims. Features from one embodiment can typically be implemented in other embodiments. By way of non-limiting example, a feature made possible by the functional fiber being used to form a sensing wearable vest (e.g., alerts, warnings, or alarms, as discussed above) can typically be carried over into other wearables, carpets, etc. as well. The disclosure of a feature in one embodiment by no means limits that feature from being incorporated into other embodiments unless explicitly stated. All publications and references cited herein are expressly incorporated herein by reference in their entirety, including references provided for in the priority patent application.

It should be noted that headings are used above for convenience and are not to be construed as limiting the present invention in any way.

The disclosed systems and methods (e.g., as in any flow charts or logic flows described above) may be implemented using computer technology and may be embodied as a computer program product for use with a computer system. Such embodiments may include a series of computer instructions fixed on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as a tangible, non-transitory semiconductor, magnetic, optical or other memory device, and may be transmitted using any communications technology, such as optical, infrared, RF/microwave, or other transmission technologies over any appropriate medium, e.g., wired (e.g., wire, coaxial cable, fiber optic cable, etc.) or wireless (e.g., through air or space).

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention may be implemented as entirely hardware, or entirely software.

Computer program logic implementing all or part of the functionality previously described herein may be executed at different times on a single processor (e.g., concurrently) or may be executed at the same or different times on multiple processors and may run under a single operating system process/thread or under different operating system processes/threads. Thus, the term "computer process" refers generally to the execution of a set of computer program instructions regardless of whether different computer processes are executed on the same or different processors and regardless of whether different computer processes run under the same operating system process/thread or different operating system processes/threads. Software systems may be implemented using various architectures such as a monolithic architecture or a microservices architecture.

Importantly, it should be noted that embodiments of the present invention may employ conventional components such as conventional computers (e.g., off-the-shelf PCs, mainframes, microprocessors), conventional programmable logic devices (e.g., off-the shelf FPGAs or PLDs), or conventional hardware components (e.g., off-the-shelf ASICs or discrete hardware components) which, when programmed or configured to perform the non-conventional methods described herein, produce non-conventional devices or systems. Thus, there is nothing conventional about the inventions described herein because even when embodiments are implemented using conventional components, the resulting devices and systems (e.g., processing systems including neural information processing systems) are necessarily non-conventional because, absent special programming or configuration, the conventional components do not inherently perform the described non-conventional functions.

The activities described and claimed herein provide technological solutions to problems that arise squarely in the realm of technology. These solutions as a whole are not well-understood, routine, or conventional and in any case provide practical applications that transform and improve computers and computer systems.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Although the above discussion discloses various exemplary embodiments of the invention, it should be apparent that those skilled in the art can make various modifications that will achieve some of the advantages of the invention without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A method for identifying activity of a subject relative the ground, the method comprising:
    receiving, by a processing system, input tactile sequence data produced from sensor signals generated by a tactile sensing floor covering, the tactile sensing floor covering comprising a piezoresistive pressure sensing matrix having a plurality of sensors and a network of orthogonal electrodes,
    wherein each sensor of the plurality of sensors is located at an overlap of the orthogonal electrodes,
    wherein the input tactile sequence data comprises sequences of tactile frames spanning respective windows of time, and
    wherein the sensor signals generated by the plurality of sensors indicate interactions of the subject with the ground during the respective windows of time;
    providing, by the processing system, the input tactile sequence data as input to a pose estimation model comprising a convolutional encoder-decoder neural network that was trained using visual data and tactile data, wherein, based on the training, the pose estimation model is configured to predict a 3D human pose based on spatiotemporal tactile information as an input, the convolutional encoder-decoder neural network comprising:
        an encoder that maps the input tactile sequence data into a 2D feature map, expands and repeats the 2D feature map to transform the 2D feature map into a 3D feature volume comprising a plurality of voxels, and appends an indexing volume channel to the 3D feature volume indicating a height of each voxel amongst the plurality of voxels; and
        a decoder that runs the appended and indexed 3D feature volume through a set of decoding layers to generate a predicted confidence map for each of a plurality of keypoints of the subject;

receiving, by the processing system and as output from the pose estimation model, the predicted confidence map for each of the plurality of keypoints of the subject;

comparing, by the processing system, the predicted confidence map for each of the plurality of keypoints of the subject with information in a database that correlates tactile information to particular activities of the subject or other subjects; and identifying, by the processing system, a particular activity of the subject based on the comparison.

2. The method of claim 1, wherein the identified activity includes at least one of an identified movement or an identified position of at least one part of the subject.

3. The method of claim 1, further comprising:
triggering, by the processing system, a notification based on the identified activity.

4. The method of claim 3, wherein the notification comprises at least one of an alarm, a warning, or an indication of an early disease detection.

5. The method of claim 1, wherein the tactile sensing floor covering comprises at least one of a carpet, rug, mat, floor cloth, pad, plank, tile, sheet, or other flooring product.

6. The method of claim 1, wherein the piezoresistive pressure sensing matrix was fabricated by aligning a network of orthogonal conductive threads as electrodes on each side of a commercial piezoresistive film to form the network of orthogonal electrodes.

7. The method of claim 1, wherein the processing system comprises a neural information processing system.

8. The method of claim 1, further comprising:
collecting tactile information for a plurality of test subjects along with reference information; and
processing the collected tactile information and the reference information to produce the information in the database that correlates the tactile information to the particular activities.

9. The method of claim 8, wherein the reference information comprises video or images of the test subjects producing the collected tactile information.

* * * * *